US012611460B2

(12) United States Patent
Chau et al.

(10) Patent No.: US 12,611,460 B2
(45) Date of Patent: *Apr. 28, 2026

(54) EYEDROP COMPOSITIONS

(71) Applicant: The Hong Kong University of Science and Technology, Hong Kong (CN)

(72) Inventors: Ying Chau, Hong Kong (CN); Yu Yu, Shenzhen (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 1051 days.

This patent is subject to a terminal disclaimer.

(21) Appl. No.: 17/277,989

(22) PCT Filed: Sep. 18, 2019

(86) PCT No.: PCT/CN2019/106432
§ 371 (c)(1),
(2) Date: Mar. 19, 2021

(87) PCT Pub. No.: WO2020/057548
PCT Pub. Date: Mar. 26, 2020

(65) Prior Publication Data
US 2021/0353759 A1 Nov. 18, 2021

Related U.S. Application Data

(60) Provisional application No. 62/734,089, filed on Sep. 20, 2018.

(51) Int. Cl.
| A61K 47/36 | (2006.01) |
| A61K 9/08 | (2006.01) |
| A61K 45/06 | (2006.01) |
| A61P 27/04 | (2006.01) |

(52) U.S. Cl.
CPC ................ *A61K 47/36* (2013.01); *A61K 9/08* (2013.01); *A61K 45/06* (2013.01); *A61P 27/04* (2018.01)

(58) Field of Classification Search
CPC .................................................... A61K 31/728
See application file for complete search history.

(56) References Cited

U.S. PATENT DOCUMENTS

| 5,128,326 | A | 7/1992 | Balazs et al. | |
| 7,939,655 | B2 | 5/2011 | Carlino | |
| 8,481,080 | B2 | 7/2013 | Longin et al. | |
| 9,844,597 | B2 | 12/2017 | Chau et al. | |
| 9,895,394 | B2 | 2/2018 | Leung et al. | |
| 12,029,753 | B2 * | 7/2024 | Chau .................... | A61K 31/728 |
| 2006/0052336 | A1 | 3/2006 | Carlino | |
| 2006/0094643 | A1 | 5/2006 | Svirkin et al. | |
| 2009/0155362 | A1 | 6/2009 | Longin et al. | |
| 2013/0338100 | A1 | 12/2013 | Longin et al. | |
| 2014/0221309 | A1 | 8/2014 | Beard et al. | |
| 2014/0328926 | A1 * | 11/2014 | Gravett .................. | A61K 45/06 |
| | | | | 514/180 |
| 2015/0087725 | A1 | 3/2015 | Chau et al. | |
| 2015/0157563 | A1 * | 6/2015 | Wirostko ........... | A61K 31/5575 |
| | | | | 424/428 |
| 2015/0190420 | A1 | 7/2015 | Longin et al. | |
| 2015/0250815 | A1 * | 9/2015 | Leung ................ | A61K 49/0008 |
| | | | | 514/59 |
| 2016/0038599 | A1 | 2/2016 | Chau et al. | |

FOREIGN PATENT DOCUMENTS

| CA | 3 015 592 | A1 | 9/2017 | | |
| CN | 1674920 | A | 9/2005 | | |
| CN | 101107270 | A | 1/2008 | | |
| CN | 102178692 | A | 9/2011 | | |
| IL | 73217 | A | 6/1991 | | |
| JP | 62-129226 | A | 6/1987 | | |
| JP | 2011-93897 | A | 5/2011 | | |
| JP | 2016-507529 | A | 3/2016 | | |
| JP | 2017523018 | A | * 8/2017 | ............. | A61P 41/00 |
| WO | WO-2012171335 | A1 | * 12/2012 | ............. | C07K 16/22 |
| WO | WO 2013/078770 | A1 | 6/2013 | | |
| WO | WO 2014/169708 | A1 | 10/2014 | | |
| WO | WO 2017/012712 | A1 | 1/2017 | | |
| WO | WO 2018/069763 | A1 | 4/2018 | | |

OTHER PUBLICATIONS

Salzillo (Carbohydrate Polymers vol. 153 pp. 275-283. Published 2016). (Year: 2016).*
Wirostko (Advances in Wound Care vol. 3 pp. 708-716 published 2014). (Year: 2014).*
Veterinary Internal Medicine Nursing Guide (Year: 2020).*
Yu (Biomacromolecules vol. 16 pp. 56-65 published 2015) (Year: 2015).*

(Continued)

*Primary Examiner* — George W Kosturko
(74) *Attorney, Agent, or Firm* — Merchant & Gould P.C.; Daniel J. Pereira

(57) ABSTRACT

An eyedrop composition, and methods of making and using the same, may include one or more hydrogel forming polymer having an intrinsic viscosity $[\eta]$ of at least 3 dL/g in the composition, wherein a concentration $C_T$ of such hydrogel forming polymer in the composition is at most about 5 mg/mL.

12 Claims, 16 Drawing Sheets

(56)  References Cited

OTHER PUBLICATIONS

International Search Report issued Dec. 18, 2019 in PCT/CN2019/106432 (submitting English translation only), 6 pages.

Yu Yu, et al., "Injectable Chemically Crosslinked Hydrogel for the Controlled Release of Bevacizumab in Vitreous: A 6-Month In Vivo Study" Translational Vision Science & Technology, vol. 4, No. 2, Mar. 10, 2015, pp. 1-11.

Yu Yu, et al., "Formulation of In Situ Chemically Cross-Linked Hydrogel Depots for Protein Release: From the Blob Model Perspective" Biomacromolecules, vol. 16, No. 1, Oct. 14, 2014, 10 pages.

Search Report issued Aug. 8, 2022, in corresponding Chinese Patent Application No. 201980061505.X (with English Translation of Category of Cited Documents). 4 pages.

Office Action issued Aug. 1, 2023, in corresponding Japanese Patent Application No. 2021-512445, 5 pages.

* cited by examiner

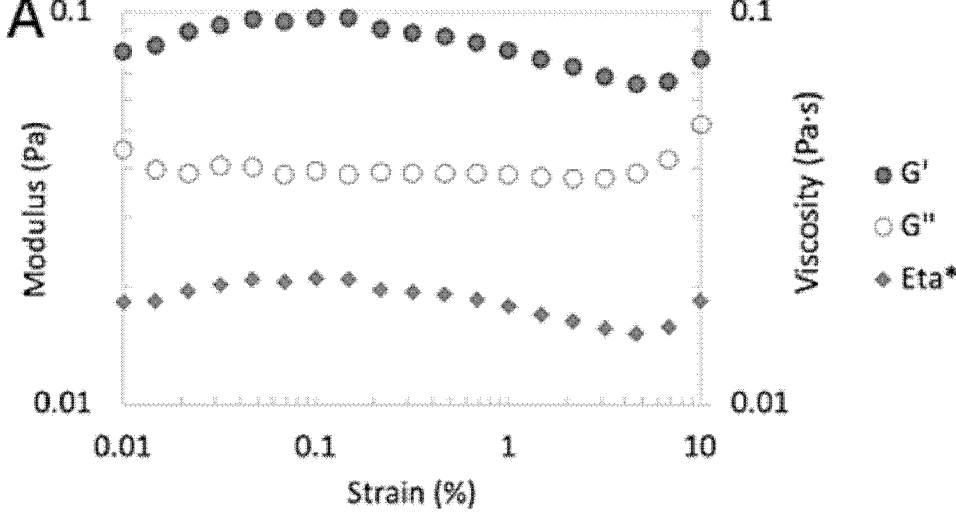
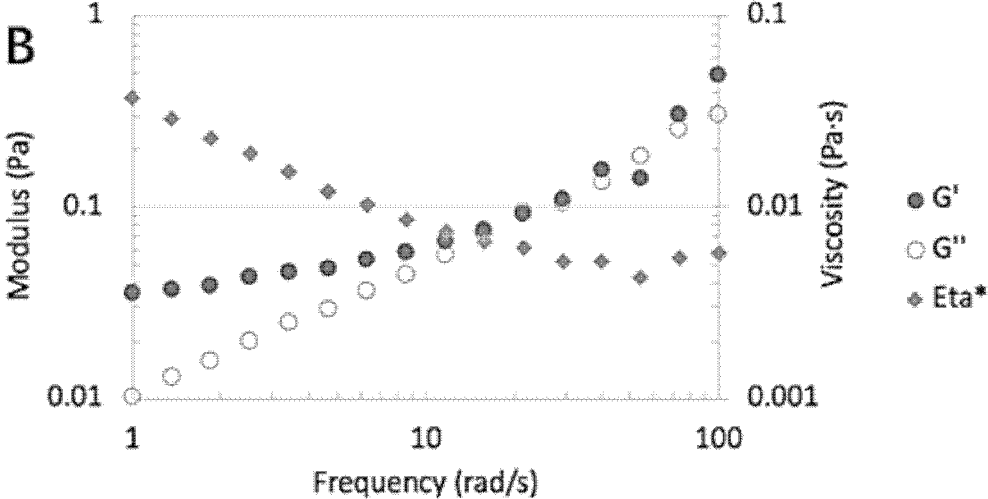
FIG. 6

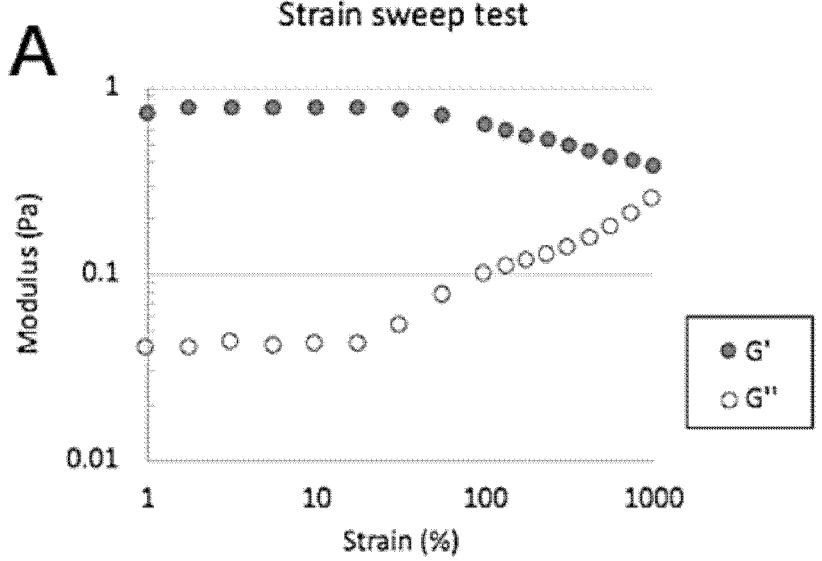
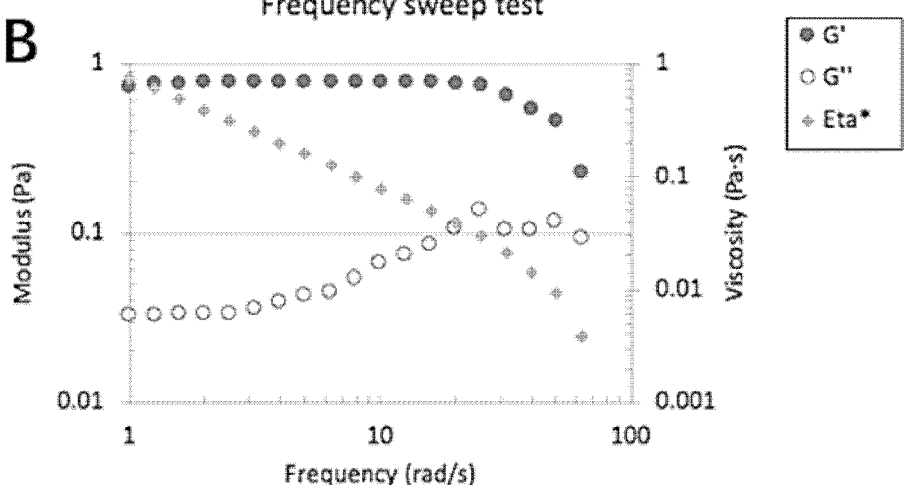
FIG. 7

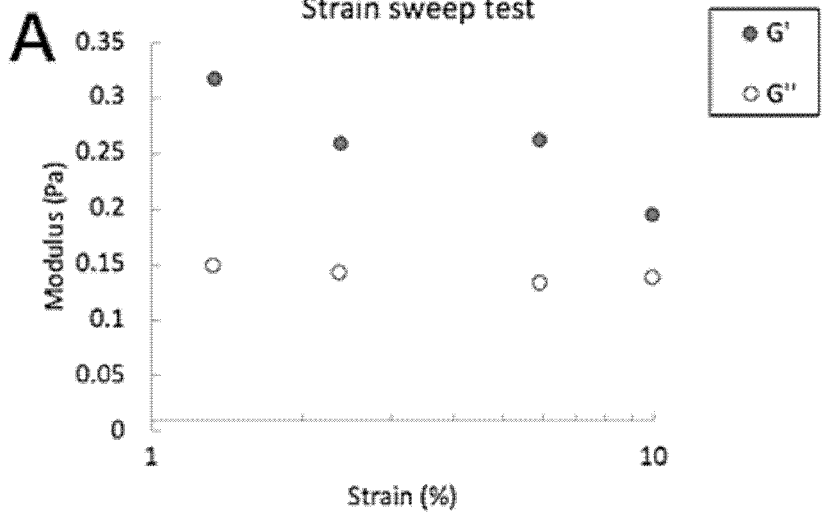
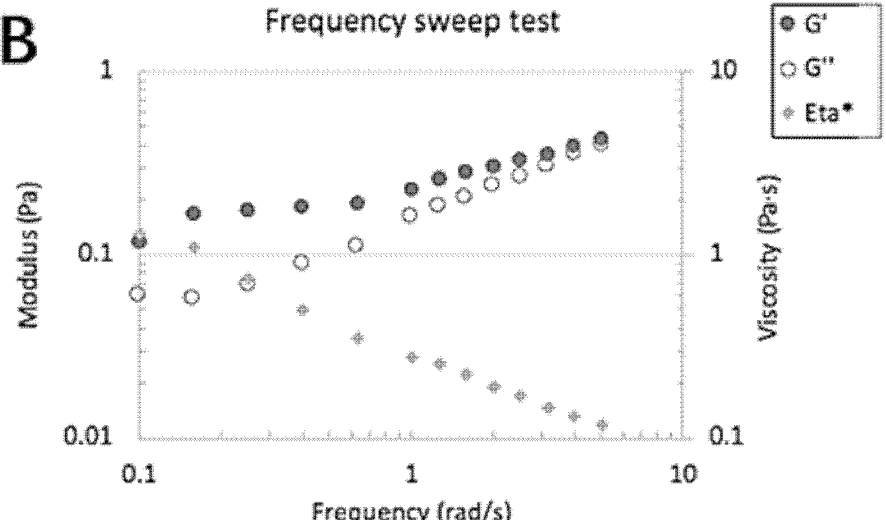
FIG. 8

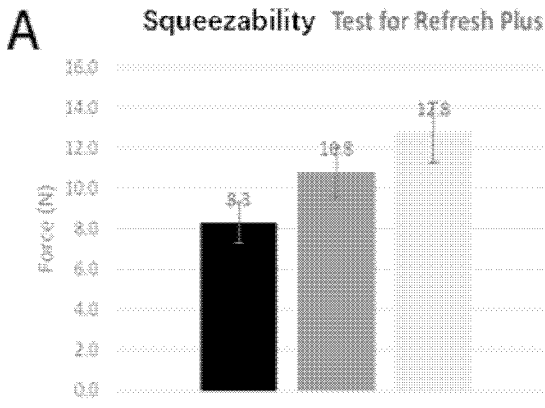
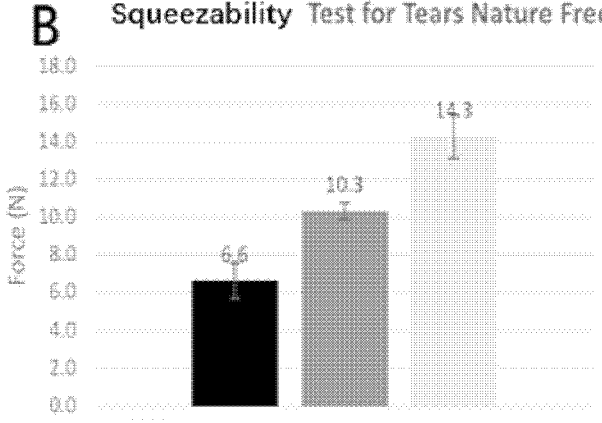
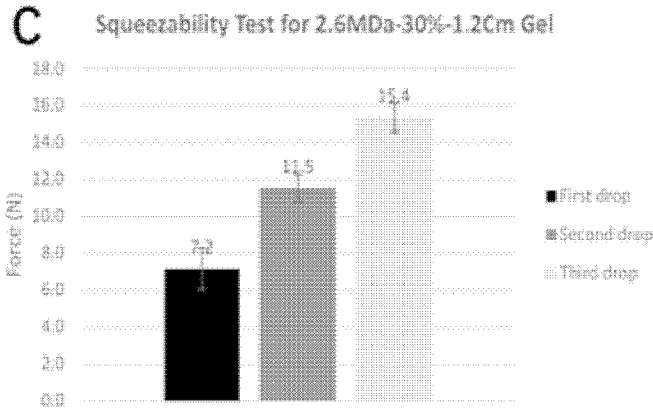
FIG. 9

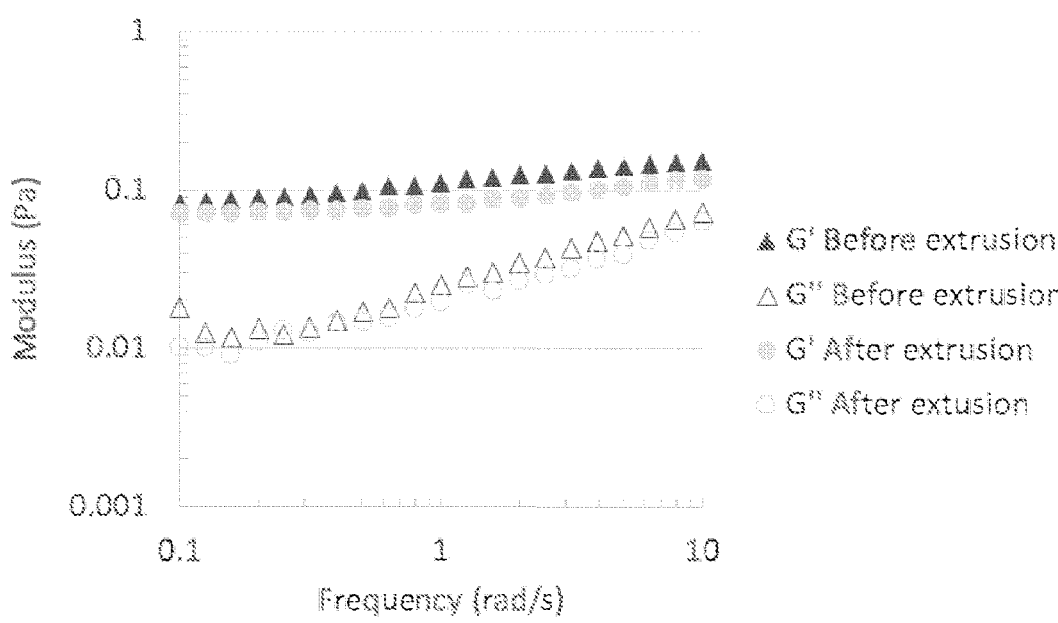
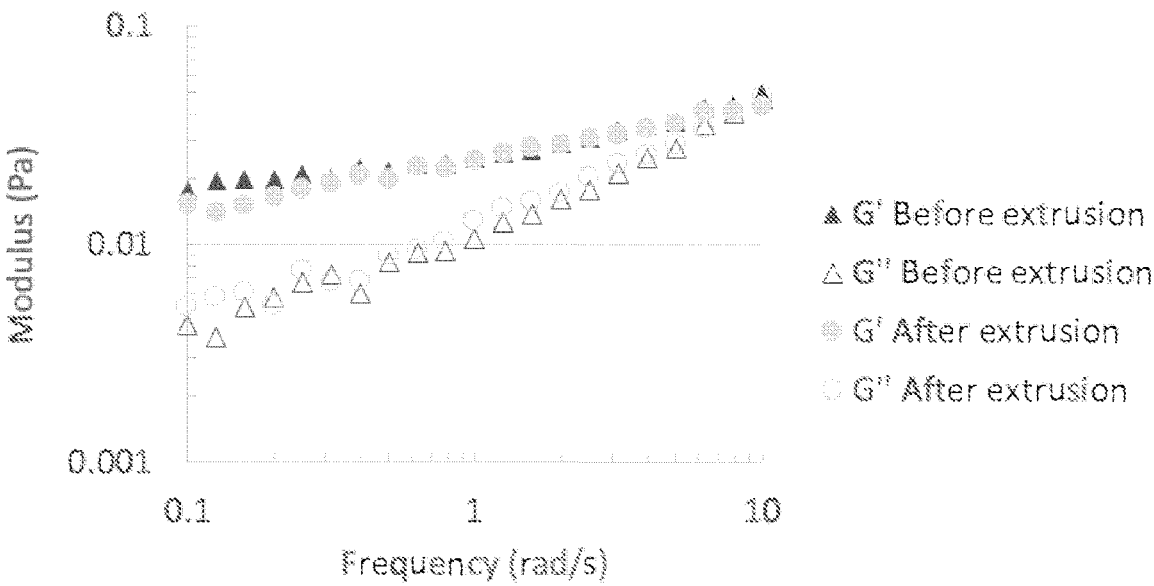
FIG. 10

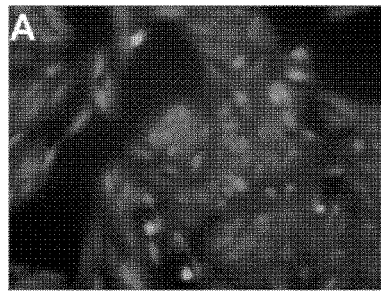 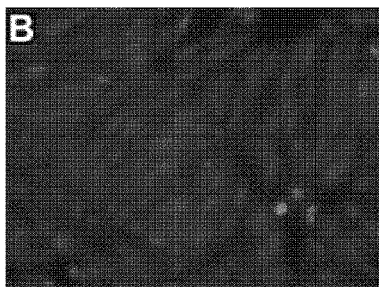 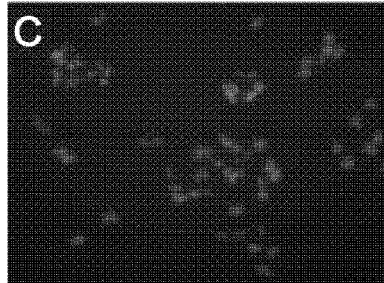

FIG. 20

Pilot Clinical Study Survey

Please kindly answer the following questions about the artificial tear:

1. Is there any irritation observed on dogs after application?
   A. Yes:_____    B. No
2. How many drops do you prefer to apply to your dog each time?
   A. 1 drop  B. 2 drops  C. 3 drops  D. More than 4 drops
3. Did you find it easy to squeeze the hydrogel out of a package?
   A. Yes, it is easy  B. No, it is difficult
4. Did the hydrogel cover most of eye surface?
   A. Yes  B. No
5. Any other comments:
   _____
   _____

FIG. 21

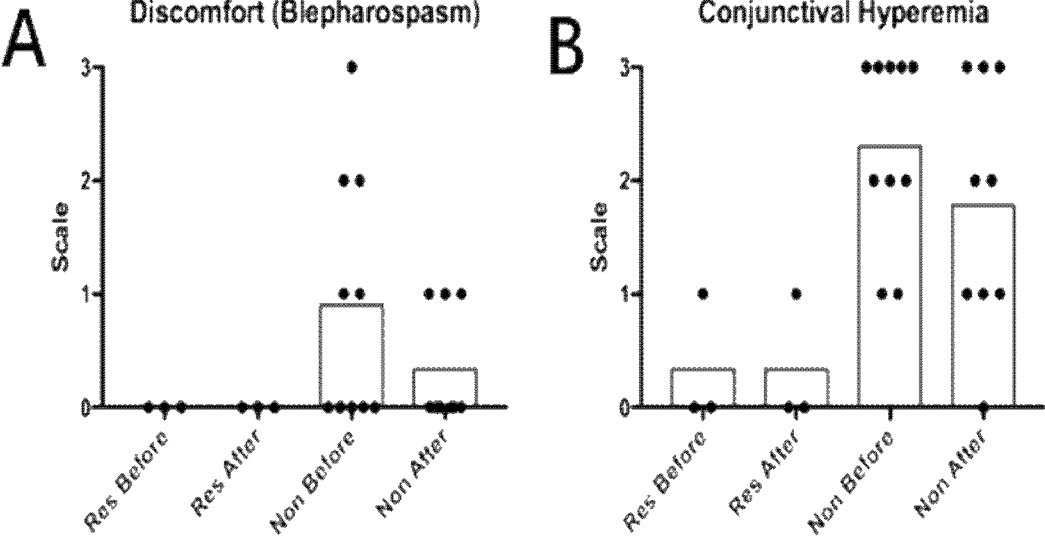
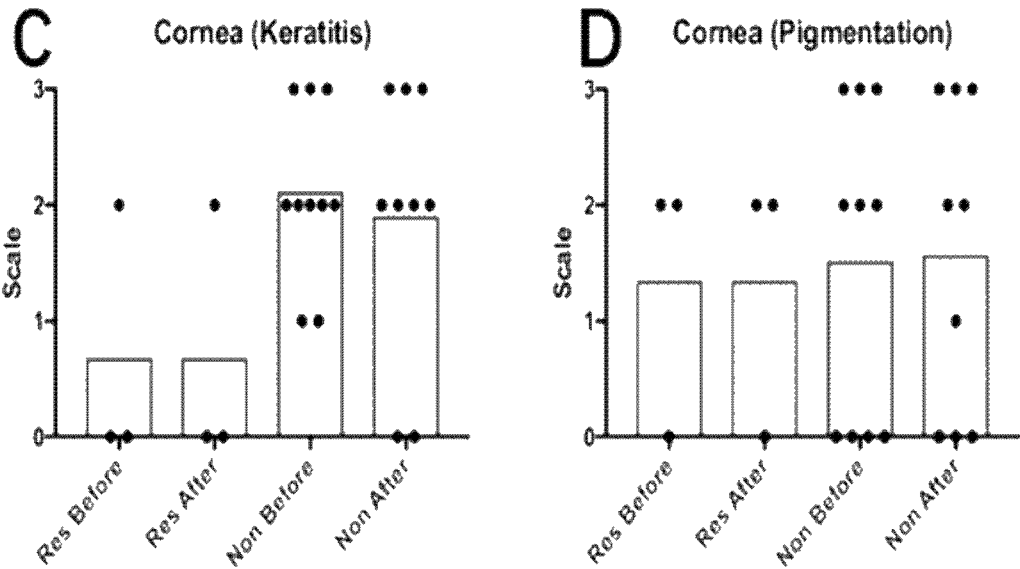
FIG. 23

EYEDROP COMPOSITIONS

CROSS-REFERENCE TO RELATED APPLICATIONS

The present application is a National Stage Application and claims priority under 35 U.S.C. § 371 to Patent Cooperation Treaty application PCT/CN2019/106432, filed Sep. 18, 2019, which claims the benefit of U.S. provisional application 62/734,089, filed Sep. 20, 2018. Priority is claimed to these applications, the entire disclosure of each of which, to the extent allowed, is incorporated by referenced herein.

BACKGROUND OF THE INVENTION

Dry eye disease (DED), is a multifactorial disease of the tears and ocular surface that results in symptoms of discomfort, visual disturbance, and tear film in stability with potential damage to ocular surface. Dry eyes are common in both humans and dogs. The prevalence of dry eye diseases in humans ranges from 7.4% to 33.7%, while the incident rate in dogs can reach up to 20%. Further, Contact Lens Discomfort (CLD) affects as much as 50% of lens wearer and is the major reason for lens ware drop out.

Artificial tear and contact lens rewetting/lubricating drops are widely used for treating dry eyes and/or CLD. However, frequent instillation is often required due to its rapid precorneal clearance by tear flow and eye blinking motion. A patient needs to apply an artificial tear for more than 6 times per day if the dryness is severe. Other forms of vehicles, including ointments and gels, have longer precorneal retention time but the irritating sensation and undesirable cosmetic outlook greatly limits their use in everyday lives.

Thus, there is a need to generate hydrogels having desired properties to be eyedrop compositions.

SUMMARY OF THE INVENTION

The present disclosure provides an eyedrop composition, comprising one or more hydrogel forming polymer having an intrinsic viscosity [η] of at least 3 dL/g in the composition (e.g., as measured by a Ubbelohde viscometer), wherein a concentration $C_T$ of the hydrogel forming polymer in the composition is at most about 5 mg/ml. The eyedrop composition could exhibit at least one of the following properties: 1) longer precorneal residence time; 2) better controlled release of drug from the eyedrop composition with longer drug action time (e.g., for 1 hour or longer); 3) better biocompatibility; 4) longer storage time; 5) good clinical trial results; 6) posing no burden in terms of squeezing force requirement. The hydrogels of the eyedrop composition according to the present disclosure may have a relatively low G' (e.g. with a G' less than about 10.0 Pa), a higher G' comparing to G" (e.g G"/G'<1) while having relatively large yield strain (e.g., ≥10%). Accordingly, the hydrogels formed according to the present disclosure are suitable for being spread on surfaces. In addition, the hydrogel of the eyedrop composition may have a low viscosity (e.g., with a complex viscosity of no more than about 0.2 Pa·s) at high shear rate, indicating that it might be easy to spread across a surface with the help of only a small force. In addition, viscosity of the hydrogel of the eyedrop composition may increase exponentially towards low shear rate, indicating that it may be stable at rest. Moreover, the hydrogel of the eyedrop composition may be able to move freely in water without dissolution and could still show this property even after prolonged (e.g., for 24 hours or longer) period of time of being soaked in water.

In one aspect, the present disclosure provides an eyedrop composition, comprising one or more hydrogel forming polymer having an intrinsic viscosity [η] of at least 3 dL/g (e.g., at least 5 dL/g, at least 8 dL/g, at least 10 dL/g, at least 12 dL/g, at least 15 dL/g, at least 16 dL/g, at least 17 dL/g, at least 18 dL/g, at least 19 dL/g, at least 20 dL/g, at least 25 dL/g, or more) in the composition, wherein a concentration $C_T$ of such hydrogel forming polymer in the composition is at most about 5 mg/ml (e.g., at most about 4 mg/ml, at most about 3 mg/ml, at most about 2 mg/ml, at most about 1.5 mg/ml, at most about 1 mg/ml, at most about 0.9 mg/ml, at most about 0.8 mg/ml, at most about 0.7 mg/ml, at most about 0.6 mg/ml, at most about 0.5 mg/ml, at most about 0.4 mg/ml, at most about 0.3 mg/ml, at most about 0.2 mg/ml, at most about 0.1 mg/ml, or less). The intrinsic viscosity [η] may be as measured by a Ubbelohde viscometer.

In some embodiments, at least some of the hydrogel forming polymers are comprised in the composition in a hydrogel formed. The hydrogel may have at least one of the followings:

1) a storage modulus G' of no more than about 10.0 Pa (e.g., no more than about 8.0 pa, no more than about 7.0 pa, no more than about 6.0 pa, no more than about 5.0 pa, no more than about 4.0 pa, no more than about 3.0 pa, no more than about 2.0 pa, no more than about 1.0 pa, no more than about 0.8 pa, no more than about 0.7 pa, no more than about 0.6 pa, no more than about 0.5 pa, or less), as measured in a dynamic oscillatory shear test;

2) a loss modulus G" of no more than about 10.0 Pa (e.g., no more than about 8.0 pa, no more than about 7.0 pa, no more than about 6.0 pa, no more than about 5.0 pa, no more than about 4.0 pa, no more than about 3.0 pa, no more than about 2.0 pa, no more than about 1.0 pa, no more than about 0.8 pa, no more than about 0.7 pa, no more than about 0.6 pa, no more than about 0.5 pa, or less), as measured in a dynamic oscillatory shear test;

3) a complex viscosity of no more than about 0.2 Pa·s (e.g., no more than about 0.1 Pa·s, no more than about 0.08 Pa·s, no more than about 0.07 Pa·s, no more than about 0.06 Pa·s, no more than about 0.05 Pa·s, or no more than about 0.04 Pa·s) as measured in a dynamic oscillatory shear test at a frequency of less than about 100 rad/s (e.g., less than about 90 rad/s, less than about 80 rad/s, less than about 70 rad/s, less than about 50 rad/s, less than about 40 rad/s, less than about 30 rad/s, less than about 20 rad/s, less than about 10 rad/s or less);

4) an extrusion force of about 4 N to about 45 N (for example, about 4 N to about 45 N, about 5 N to about 45 N, about 6 N to about 45 N, about 7 N to about 45 N, about 8 N to about 45 N, about 9 N to about 45 N, about 10 N to about 45 N, about 12 N to about 45 N, about 15 N to about 45 N, about 20 N to about 45 N, about 25 N to about 45 N, about 30 N to about 45 N, about 35 N to about 45 N, or about 40 N to about 45 N), when the hydrogel is squeezed out of a Tears Naturale Free 0.6 ml blow-fill-seal (BFS) single use bottle; and 5) a yield strain of at least about 10% (e.g. at least about 10%, 9%, 8%, 7%, 6%, 5%, 4%, 3%, 2%, 1%, 0.5%, 0.2%, or 0.1%), as measured in a dynamic oscillatory strain sweep test.

In some embodiments, the hydrogel has a loss modulus G" that is no more than about 100% of its storage modulus G', as measured in a dynamic oscillatory shear test.

In some embodiments, the polymer is hydrophilic and/or water soluble.

In some embodiments, the polymer is selected from the group consisting of a polysaccharide, a poly acrylic acid, a poly hydroxyethylmethacrylate, an elastin, a collagen, a derivative thereof, and any combinations thereof.

In some embodiments, the polymer is selected from the group consisting of a hyaluronic acid, a guar gum, a starch, a chitosan, a chondroitin sulfate, an alginate, a carboxymethylcellulose, a derivative thereof, and any combinations thereof.

In some embodiments, the polymer is selected from the group consisting of a hyaluronic acid, a derivative thereof, and any combinations thereof.

In some embodiments, the polymer comprises a derivative modified with one or more modifications selected from the group consisting of an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol, an amine, and any combinations thereof.

In some embodiments, the derivative has an average degree of modification (DM) of about 3% to about 50% (e.g., about 4% to about 45%, about 5% to about 40%, about 6% to about 40%, about 7% to about 40%, about 8% to about 39%, about 8% to about 38%, about 8% to about 35%, about 9% to about 32%, about 8% to about 30%, about 10% to about 30%, about 12% to about 30%, about 13% to about 30%, about 14% to about 30%, about 15% to about 35%, or about 15% to about 30%).

In some embodiments, the eyedrop composition comprises at least a first polymer derivative and a second polymer derivative, wherein the first polymer derivative comprises a first modification and the second polymer derivative comprises a second modification, the first modification is different from the second modification, and the first polymer derivative is capable of reacting with the second polymer derivative to form the hydrogel.

In some embodiments, a mass ratio between the first polymer derivative and the second polymer derivative in the composition is from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10).

In some embodiments, a molar ratio between the first polymer derivative and the second polymer derivative in the composition is from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10).

In some embodiments, a volume ratio between the first polymer derivative and the second polymer derivative in the composition is from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10).

In some embodiments, the first polymer derivative has a first DM, the second polymer derivative has a second DM, and a ratio between the first DM and the second DM is from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10).

In some embodiments, the first modification and the second modification are each independently selected from the group consisting of an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol, an amine, and any combinations thereof.

In some embodiments, the one or more polymers are hyaluronic acid derivatives, the first polymer derivative is a hyaluronic acid modified with one or more vinylsulfone groups, the second polymer derivative is a hyaluronic acid modified with one or more thiol groups, and wherein the first polymer derivative is capable of reacting with the second polymer derivative to form the hydrogel.

In some embodiments, the polymer has an average molecular weight from about 100,000 to about 5,000,000 dalton (e.g., from about 120,000 to about 5,000,000 dalton, from about 200,000 to about 5,000,000 dalton, from about 300,000 to about 5,000,000 dalton, from about 400,000 to about 5,000,000 dalton, from about 500,000 to about 5,000,000 dalton, from about 600,000 to about 5,000,000 dalton, from about 670,000 to about 5,000,000 dalton, from about 1,000,000 to about 5,000,000 dalton, from about 1,500,000 to about 5,000,000 dalton, from about 2,000,000 to about 5,000,000 dalton, from about 2,500,000 to about 5,000,000 dalton, from about 2,600,000 to about 5,000,000 dalton, from about 3,000,000 to about 5,000,000 dalton, from about 3,500,000 to about 5,000,000 dalton, from about 3,600,000 to about 5,000,000 dalton, from about 2,000,000 to about 4,000,000 dalton, from about 2,500,000 to about 3,500,000 dalton, from about 2,600,000 to about 3,600,000 dalton, from about 1,000,000 to about 2,600,000 dalton, from about 800,000 to about 2,600,000 dalton, from about 700,000 to about 2,500,000 dalton, from about 670,000 to about 2,600,000 dalton, or from about 600,000 to about 2,500,000 dalton).

In some embodiments, the eyedrop composition further comprises a cross-linker different from the one or more polymers (e.g., a crosslinker different from the polymers in the composition), wherein the cross-linker is a small molecule cross-linker, a macromolecule cross-linker, or a combination thereof.

In some embodiments, the cross-linker is a small molecule cross-linker comprising a molecule containing a group selected from acrylate, maleimide, vinylsulfone, hydroxysuccinimide, aldehyde, ketone, multi-carbodiimide, carbonate, iodoacetyl, mercaptonicotinamide, quinone, thiol, amine, and any combinations thereof.

In some embodiments, the cross-linker is a macromolecule cross-linker comprising a macromolecule containing a group selected from acrylate, maleimide, vinylsulfone, hydroxysuccinimide, aldehyde, ketone, multi-carbodiimide, carbonate, iodoacetyl, mercaptonicotinamide, quinone, thiol, amine, and any combinations thereof.

In some embodiments, the cross-linker is selected from the group consisting of dithiothreitol, di-cysteine, PEG-dithiol, 4 or 8 arm-PEG thiol, divinyl sulfone, Bis(vinylsulfonyl)methane, PEG-VS and 4 or 8 arm-PEGVS.

In some embodiments, the eyedrop composition does not comprise a crosslinker different from the one or more polymers.

In some embodiments, the eyedrop composition comprises a phosphate buffer.

In some embodiments, the eyedrop composition having a pH of about 3.5 to about 9.0 (e.g., about 4.0 to about 9.0, about 4.5 to about 9.0, about 5.0 to about 9.0, about 5.5 to about 9.0, about 6.0 to about 9.0, about 6.5 to about 9.0, about 7.0 to about 9.0, about 7.5 to about 9.0, about 8.0 to about 9.0, about 8.5 to about 9.0, about 7.0 to about 7.8, or about 7.4).

In some embodiments, the hydrogel is biocompatible.

In some embodiments, the eyedrop composition is an artificial tear, a contact lens rewetting agent, or a lubricating agent.

In some embodiments, the eyedrop composition further comprises a therapeutically active agent.

In another aspect, the present disclosure provides a method for treating or alleviating an eye disorder or condition in a subject in need thereof, comprising administering to the subject an effective amount of the eyedrop composition.

In some embodiments, the eye disorder or condition is selected from the group consisting of a dry eye syndrome and Contact Lens Discomfort.

In another aspect, the present disclosure provides a method for improving ocular comfort or relieving ocular dryness in a subject in need thereof, comprising administering to the subject an effective amount of the eyedrop composition.

In another aspect, the present disclosure provides use of an eyedrop composition in the manufacture of a product for treating or alleviating an eye disorder or condition.

In some embodiments, eye disorder or condition is selected from the group consisting of a dry eye syndrome and Contact Lens Discomfort.

In another aspect, the present disclosure provides use of an eyedrop composition in the manufacture of a product for improving ocular comfort or relieving ocular dryness.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

FIG. 1 illustrates the synthesis of HA-VS polymer;

FIG. 2 illustrates the synthesis of HA-SH polymer;

FIG. 3 illustrates the synthesis of the hydrogel of the present disclosure;

FIGS. 6A and 6B illustrate the modulus and complex viscosity of the hydrogel of the present disclosure;

FIGS. 7A and 7B illustrate the strain sweep test and frequency sweep test of the hydrogel of the present disclosure;

FIGS. 8A and 8B illustrate the strain sweep test and frequency sweep test of the hydrogel of the present disclosure;

FIGS. 9A~9C illustrate the force requirements for squeezing the hydrogel/eye composition of the present disclosure out from a container;

FIG. 10 illustrates the G' and G" of the hydrogel of the present disclosure before and after destruction;

FIGS. 20A~20C illustrate the in-vitro biocompatibility of the eyedrop composition of the present disclosure;

FIG. 21 illustrates the survey questions distributed to pet owners for subjective assessment of the eyedrop composition of the present disclosure;

DETAILED DESCRIPTION

Figure 4:
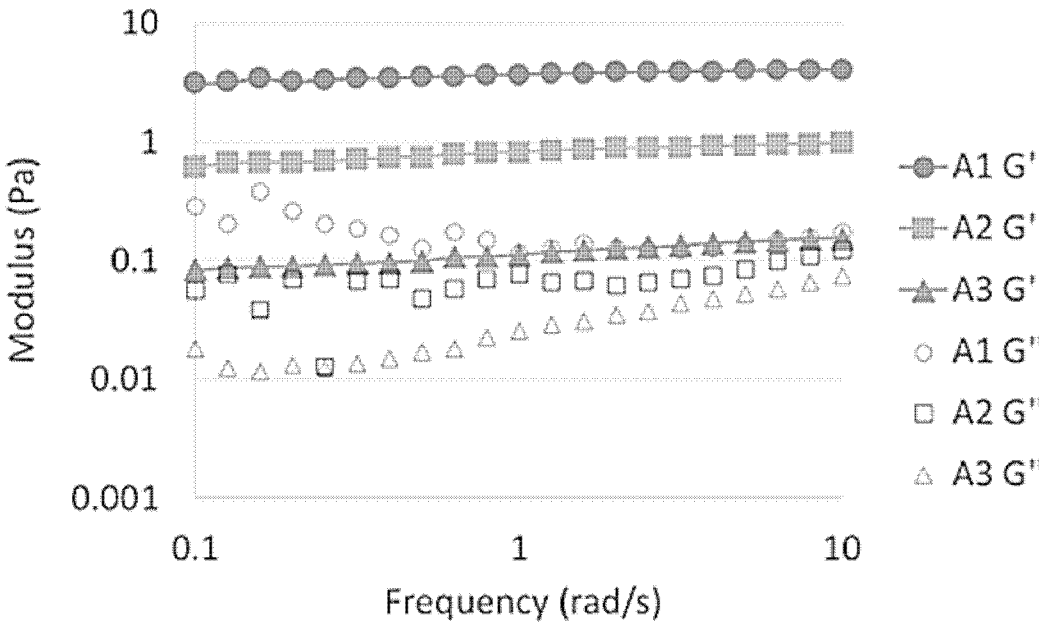
FIG. 4 illustrates the modulus of the hydrogel of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "polymer", as used herein, generally refers to a chemical compound or mixture of compounds formed by polymerization and consisting essentially of repeating structural units.

The term "hydrogel", as used herein, generally refers to a gel or gel-like structure comprising one or more polymers suspended in an aqueous solution (e.g., water).

The term "viscosity", as used herein, generally refers to a property of resistance to flow in a fluid or semifluid.

The term "intrinsic viscosity", as used herein, generally refers to a measure of a substance's (e.g., a polymer) contribution to the viscosity of a system (e.g., a solution). In the present disclosure, the intrinsic viscosity $[\eta]$ may be measured by a Ubbelohde viscometer, or a differential viscometer. Alternatively, the intrinsic viscosity [η] may be calculated from Mark-Houwink equation from established relation between intrinsic viscosity and molecular weight.

The term "hydrogel forming polymer", as used herein, generally refers to a polymer participating in the formation of a hydrogel. It may be a naturally occurring polymer or a synthetic polymer capable of forming a hydrogel. The hydrogel forming polymer may include polymer(s) making a contribution to hydrogel formation. In some embodiments, the hydrogel forming polymer does not include polymers that are not able to participate in hydrogel formation, and/or polymers unable to form a hydrogel, even if present in the eyedrop composition of the present disclosure. In some cases, the hydrogel forming polymer may also be referred to as "a backbone polymer".

The term "$C_T$", as used herein, generally refers to the total concentration of a polymer or polymers in a composition. For example, $C_T$ of the hydrogel forming polymer may refer to the total concentration of the polymers forming and/or formed the hydrogel of the present disclosure. For instance, it may refer to the total concentration of the hydrogel forming polymers present in the eyedrop composition of the present disclosure. In some cases, the eyedrop composition of the present disclosure may comprise hydrogel forming polymers that have already formed the hydrogel, and/or hydrogel forming polymers that have not yet been incorporated in a hydrogel, and $C_T$ of the hydrogel forming polymers may refer to the total concentration of the hydrogel forming polymers present in the eyedrop composition (e.g., including both the polymers already incorporated in the hydrogel and those not yet incorporated). In another example, $C_T$ of the hydrogel forming polymers having an intrinsic viscosity [η] of at least 3 dL/g, may refer to the total concentration of the hydrogel forming polymers that have an intrinsic viscosity [η] of at least 3 dL/g.

The term "eyedrop composition", as used herein, generally refers to an eyedrop product (for instance, in a liquid state) of various elements or ingredients. For example, the eyedrop composition may comprise the hydrogel formed by one or more polymers, and the eyedrop composition can be extruded from the container. In some cases, the eyedrop composition may comprise the hydrogel forming polymer.

The term "storage modulus G'", as used herein, generally refers to the stored energy as measured, representing the elastic portion.

The term "loss modulus G''", as used herein, generally refers to the lost energy as measured, representing the viscous portion.

The term "extrusion force", as used herein, generally refers to a force required to extrude a material out of a container. For example, the force required to squeeze a composition or hydrogel of the present disclosure out of a bottle.

The term "yield strain", as used herein, generally refers to the strain at which a material begins to deform plastically whereas yield point is the point where nonlinear (elastic and plastic) deformation begins. Prior to the yield point, the material will deform elastically and will return to its original shape when the applied stress is removed.

The term "hydrophilic", as used herein, generally refers to having an affinity for water, able to absorb or be wetted by water. A hydrophilic molecule or portion of a molecule is one whose interactions with water and other polar substances are more thermodynamically favorable than their interactions with oil or other hydrophobic solvents.

The term "average degree of modification (DM)", as used herein, generally refers to the percentage of repeating units with pendant group in a polymer. DM may reflect the degrees of modification of hydrogel forming polymer derivative.

The term "cross-linker", as used herein, generally refers to an agent that links one polymer chain to another with bonds. The cross-linker can achieve crosslink through covalent bonds or noncovalent bonds. The "polymer chains" may refer to synthetic polymers or natural polymers (such as proteins). In polymer chemistry, when a synthetic polymer is the to be "cross-linked", it usually means that the entire bulk of the polymer has been exposed to the cross-linking method. The resulting modification of mechanical properties depends strongly on the cross-link density. Crosslinks may be formed by chemical reactions that are initiated by heat, pressure, change in pH, or radiation.

The term "eye disorder or condition", as used herein, generally refers to eye diseases and disorders thereof. The eye disorder or condition can be selected from a group consisting of but not limited to red eyes, night blindness, amblyopia, strabismus, nystagmus, colorblindness, uveitis, presbyopia, floaters, dry eyes, excess tearing, cataracts, glaucoma, retinal disorders (e.g. age-related macular degeneration, diabetic retinopathy, retinal detachment), conjunctivitis, corneal diseases, eyelid problems, vision changes and problems with contact lenses. In some cases, the eye disorder or condition may be dry eye syndrome and/or Contact Lens Discomfort.

The term "biocompatible", as used herein, generally refers to condition of being compatible with a living tissue or a living system by not being toxic, injurious, or physiologically reactive and/or not causing immunological rejection.

The term "about", when used in the context of numerical values, generally refers to a value less than 1% to 15% (e.g., less than 1%, less than 2%, less than 3%, less than 4%, less than 5%, less than 6%, less than 7%, less than 8%, less than 9%, less than 10%, less than 11%, less than 12%, less than 13%, less than 14%, or less than 15%) above or below an indicated value.

Where a range of values (e.g., a numerical range) is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein, the singular forms "a," "and," and "the" include plural referents unless the context clearly dictates otherwise. Thus, for example, reference to "a particle" includes a plurality of such particles and reference to "the sequence" includes reference to one or more the sequences and equivalents thereof known to those skilled in the art, and so forth.

As will be understood by those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

The present disclosure provides an eyedrop composition and the method for treating or alleviating the eye disorder or conditions using this composition as well as methods for making and using the same. More specifically, the present disclosure provides compositions comprising a polymer capable of forming a hydrogel, and methods for making and using the same.

In one aspect, the present disclosure provides an eyedrop composition. The eyedrop composition may comprise one or more hydrogel forming polymer(s). Such hydrogel forming polymers may have an intrinsic viscosity [η] of at least 3 dL/g (e.g., at least about 5 dL/g, at least about 8 dL/g, at least about 10 dL/g, at least about 12 dL/g, at least about 15 dL/g, at least about 16 dL/g, at least about 17 dL/g, at least about 18 dL/g, at least about 19 dL/g, at least about 20 dL/g, at least about 25 dL/g, or more) in the composition. For example, as measured by a Ubbelohde viscometer. In some embodiments, the intrinsic viscosity [η] is measured by a differential viscometer. Alternatively, the intrinsic viscosity [η] may be calculated from Mark-Houwink equation from established relation between intrinsic viscosity and molecular weight.

The total concentration of the hydrogel forming polymer(s) (e.g., of those hydrogel forming polymers having an intrinsic viscosity [η] of at least 3 dL/g) in the composition is $C_T$. The $C_T$ may be at most about 5 mg/ml (e.g., at most about 4 mg/ml, at most about 3 mg/ml, at most about 2 mg/ml, at most about 1.5 mg/ml, at most about 1 mg/ml, at most about 0.9 mg/ml, at most about 0.8 mg/ml, at most about 0.7 mg/ml, at most about 0.6 mg/ml, at most about 0.5 mg/ml, at most about 0.4 mg/ml, at most about 0.3 mg/ml, at most about 0.2 mg/ml, at most about 0.1 mg/ml, or less). For example, the $C_T$ may be about 0.05 mg/ml to about 5 mg/ml (e.g., about 0.1 mg/ml to about 5 mg/ml, about 0.2 mg/ml to about 5 mg/ml, about 0.3 mg/ml to about 5 mg/ml, about 0.4 mg/ml to about 5 mg/ml, about 0.5 mg/ml to about 5 mg/ml, about 0.6 mg/ml to about 5 mg/ml, about 0.7 mg/ml to about 5 mg/ml, about 0.8 mg/ml to about 5 mg/ml, about 0.9 mg/ml to about 5 mg/ml, about 1.0 mg/ml to about 5 mg/ml, about 1.0 mg/ml to about 4 mg/ml, about 1.0 mg/ml to about 3 mg/ml, about 1.0 mg/ml to about 2 mg/ml, about 0.3 mg/ml to about 0.8 mg/ml, about 0.3 mg/ml to about 0.6 mg/ml, or about 0.3 mg/ml to about 0.5 mg/ml).

For example, the eyedrop composition may comprise various polymers, some of them are able to participate in hydrogel formation (e.g., the hydrogel forming polymers). Among the hydrogel forming polymers, some have an intrinsic viscosity [η] of at least 3 dL/g, and the total concentration $C_T$ of those hydrogel forming polymers having an intrinsic viscosity [η] of at least 3 dL/g may be at most about 5 mg/ml (e.g., at most about 4 mg/ml, at most about 3 mg/ml, at most about 2 mg/ml, at most about 1.5 mg/ml, at most about 1 mg/ml, at most about 0.9 mg/ml, at most about 0.8 mg/ml, at most about 0.7 mg/ml, at most about 0.6 mg/ml, at most about 0.5 mg/ml, at most about 0.4 mg/ml, at most about 0.3 mg/ml, at most about 0.2 mg/ml, at most about 0.1 mg/ml, or less). For example, the total concentration $C_T$ of those hydrogel forming polymers having an intrinsic viscosity [η] of at least 3 dL/g may be about 0.05 mg/ml to about 5 mg/ml (e.g., about 0.1 mg/ml to about 5 mg/ml, about 0.2 mg/ml to about 5 mg/ml, about 0.3 mg/ml to about 5 mg/ml, about 0.4 mg/ml to about 5 mg/ml, about 0.5 mg/ml to about 5 mg/ml, about 0.6 mg/ml to about 5 mg/ml, about 0.7 mg/ml to about 5 mg/ml, about 0.8 mg/ml to about 5 mg/ml, about 0.9 mg/ml to about 5 mg/ml, about 1.0 mg/ml to about 5 mg/ml, about 1.0 mg/ml to about 4 mg/ml, about 1.0 mg/ml to about 3 mg/ml, about 1.0 mg/ml to about 2 mg/ml, about 0.3 mg/ml to about 0.8 mg/ml, about 0.3 mg/ml to about 0.6 mg/ml, or about 0.3 mg/ml to about 0.5 mg/ml).

In some cases, initially, the hydrogel forming polymers in the eyedrop composition may exist in non-crosslinked forms (e.g., the hydrogel has not been formed yet), and after certain treatment (e.g., after being incubated under for example, 37° C. for a certain period of time, e.g., 12 hours or longer), some of the hydrogel forming polymers may be chemically and/or physically crosslinked to form the hydrogel. In certain embodiments, almost all the hydrogel forming polymers are chemically and/or physically crosslinked to form the hydrogel.

Thus, in some cases, the eyedrop composition may comprise hydrogels that have been formed. In such cases, at least some of the hydrogel forming polymers are comprised in the composition in the hydrogel formed. For example, the hydrogel forming polymers in the eyedrop composition may comprise both polymers that have already formed the hydrogel, and polymers that have not yet been incorporated in a hydrogel but are capable of forming a hydrogel under certain reaction conditions (e.g., after being incubated under 37° C. for a period of time, e.g., 12 h). In such cases, the total concentration $C_T$ of both the hydrogel forming polymers already comprised in the hydrogel and those not yet incorporated in the hydrogel may be at most about 5 mg/ml.

In some cases, almost all the hydrogel forming polymers in the eyedrop composition may have formed the hydrogel (e.g., through chemical and/or physical crosslinking).

The hydrogel according to the present disclosure may have one or more specific characteristics/properties.

For example, the hydrogel may have a storage modulus G' of no more than about 10.0 Pa (e.g., no more than about 8.0 pa, no more than about 7.0 pa, no more than about 6.0 pa, no more than about 5.0 pa, no more than about 4.0 pa, no more than about 3.0 pa, no more than about 2.0 pa, no more than about 1.0 pa, no more than about 0.8 pa, no more than about 0.7 pa, no more than about 0.6 pa, no more than about 0.5 pa, or less), as measured in a dynamic oscillatory shear test.

The hydrogel of the present disclosure may have a loss modulus G" of no more than about 10.0 Pa (e.g., no more than about 8.0 pa, no more than about 7.0 pa, no more than about 6.0 pa, no more than about 5.0 pa, no more than about 4.0 pa, no more than about 3.0 pa, no more than about 2.0 pa, no more than about 1.0 pa, no more than about 0.8 pa, no more than about 0.7 pa, no more than about 0.6 pa, no more than about 0.5 pa, or less), as measured in a dynamic oscillatory shear test.

The hydrogel of the present disclosure may have a complex viscosity of no more than about 0.2 Pa·s (e.g., no more than about 0.1 Pa·s, no more than about 0.08 Pa·s, no more than about 0.07 Pa·s, no more than about 0.06 Pa·s, no more than about 0.05 Pa·s, or no more than about 0.04 Pa·s) as measured in a dynamic oscillatory shear test at a frequency of less than about 100 rad/s (e.g., less than about 90 rad/s, less than about 80 rad/s, less than about 70 rad/s, less than about 50 rad/s, less than about 40 rad/s, less than about 30 rad/s, less than about 20 rad/s, less than about 10 rad/s or less).

The hydrogel of the present disclosure may have an extrusion force of about 4 N to about 45 N (for example, about 4 N to about 45 N, about 5 N to about 45 N, about 6 N to about 45 N, about 7 N to about 45 N, about 8 N to about 45 N, about 9 N to about 45 N, about 10 N to about 45 N, about 12 N to about 45 N, about 15 N to about 45 N, about 20 N to about 45 N, about 25 N to about 45 N, about 30 N to about 45 N, about 35 N to about 45 N, or about 40 N to about 45 N), when the hydrogel is squeezed out of a bottle (such as a Tears Naturale Free 0.6 ml blow-fill-seal (BFS) single use bottle).

The hydrogel of the present disclosure may have a yield strain of at least about 10% (for example, at least about 10%, at least about 11%, at least about 12%, at least about 13%, at least about 14%, at least about 15%, at least about 16%, at least about 17%, at least about 18%, at least about 19%, at least about 20%, at least about 50%, at least about 80% or more), as measured in a dynamic oscillatory strain sweep test.

For example, in the dynamic oscillatory shear test, a sinusoidal force (e.g., a stress) may be applied to a material and the resulting displacement (strain) may be measured. For a perfectly elastic solid, the resulting strain and the stress may be perfectly in phase. For a purely viscous fluid, there may be a 90 degree phase lag of strain with respect to stress. Viscoelastic polymers having characteristics in between may have a phase lag during the test, and the storage modulus may be calculated accordingly.

The extrusion force may be tested by forcing (e.g. squeezing) the eyedrop composition (e.g., comprising the hydrogel of the present disclosure) out of a container, such as an eyedrop bottle. The eyedrop bottle may have a volume of at least about 0.1 ml (e.g., at least about 0.2 ml, at least about 0.3 ml, at least about 0.4 ml, at least about 0.5 ml, at least about 0.6 ml, at least about 0.7 ml, at least about 0.8 ml, at least about 0.9 ml, at least about 1.0 ml, at least about 1.1 ml, at least about 1.2 ml, at least about 1.3 ml, at least about 1.4 ml, at least about 1.5 ml, at least about 2.0 ml, or more). The eyedrop bottle may be made from a material selected from the group consisting of: PET, Acetal, HDPE, LDPE, Nylon, PBT, PEEK, Polypropylene, PPS, PTFE, PVDF and UHMW-PE. The eyedrop bottle may have a Caliber of at least about 0.01 mm (e.g., at least about 0.05 mm, at least about 0.1 mm, at least about 0.15 mm, at least about 0.2 mm, at least about 0.25 mm, at least about 0.3 mm, at least about 0.35 mm, at least about 0.4 mm, at least about 0.45 mm, at least about 0.5 mm, at least about 0.55 mm, at least about 0.6 mm, at least about 0.7 mm, at least about 0.8 mm, at least about 0.9 mm, at least about 1.0 mm, or larger). The eyedrop bottle may have a screw cap, a needle cap, or other suitable types of cap. In some embodiments, the eyedrop bottle is a Tears Naturale Free 0.6 ml blow-fill-seal (BFS) single use bottle.

A dynamic mechanical analyzer (DMA) may be used to measure the storage modulus and may be used in a dynamic oscillatory shear test. In another example, a DMA analyzer may comprise a displacement sensor (such as a linear variable differential transformer), which may measure a change in voltage as a result of the instrument probe moving through a magnetic core. The DMA analyzer may further comprise a temperature control system or furnace, a drive motor (e.g., a linear motor for probe loading which may provide load for the applied force), a drive shaft support and a guidance system to act as a guide for the force from the motor to the sample, and one or more sample clamps in order to hold the sample being tested.

Different types of DMA analyzers may be used. For example, a forced resonance analyzer or a free resonance analyzer may be used. A free resonance analyzer may measure the free oscillations of damping of a sample being tested by suspending and swinging the sample. A forced resonance analyzer may force the sample to oscillate at a certain frequency and may be reliable for performing a temperature sweep. The analyzers may be made for both stress (force) and strain (displacement) control. For example, in strain control, the probe may be displaced, and the resulting stress of the sample may be measured by implementing a force balance transducer, which may utilize different shafts. In stress control, a set force may be applied, and several other experimental conditions (temperature, frequency, or time) may be varied. The stress and strain may be applied via torsional or axial analyzers. With a torsional analyzer, the force is applied in a twisting motion. An axial analyzer may be used for flexure, tensile, and/or compression testing.

A variety of test modes may be employed to probe the viscoelastic properties of polymers, such as temperature sweep testing, frequency sweep testing, strain sweep testing, or a combination thereof. For example, in a strain sweep testing, by gradually increasing the amplitude of oscillations, a strain sweep measurement may be performed. The variation of storage and loss moduli with increasing strain may be used for material characterization, and to determine the upper bound of a material's linear stress-strain regime.

A variety of mechanical properties can be determined by DMA. These properties include storage modulus (G'), loss modulus (G"), complex modulus (G*), loss angle (tan ($\delta$)), complex viscosity ($\eta^*$), it's in phase ($\eta'$) and out of phase component ($\eta''$), complex compliance (J*), storage compliance (J'), loss compliance (J") etc.

In some cases, the hydrogel may have a loss modulus G" that is no more than about 100% (for example, no more than about 100%, no more than about 90%, no more than about 80%, no more than about 70%, no more than about 60%, no more than about 50%, no more than about 40%, no more than about 30%, no more than about 20%, no more than about 10%, no more than about 5%, no more than about 3%, no more than about 2%, no more than about 1% or less) of its storage modulus G', as measured in a dynamic oscillatory shear test.

In some cases, the polymer may be hydrophilic and/or water soluble.

In some cases, the polymer (e.g., the hydrogel forming polymers) may be selected from the group consisting of a polysaccharide, a poly acrylic acid, a poly hydroxyethylmethacrylate, an elastin, a collagen, a derivative thereof, and any combinations thereof. For example, the polymers (e.g., the hydrogel forming polymers) in the eyedrop composition may comprise one or more of the following: a polysaccharide, one or more types of poly acrylic acid derivative, a poly hydroxyethylmethacrylate, one or more types of poly hydroxyethylmethacrylate derivative, an elastin, one or more types of elastin derivative, a collagen and one or more types of collagen derivative.

In some cases, the polymer (e.g., the hydrogel forming polymers) may be selected from the group consisting of a hyaluronic acid, a guar gum, a starch, a chitosan, a chondroitin sulfate, an alginate, a carboxymethylcellulose, a derivative thereof, and any combinations thereof. For example, the polymers (e.g., the hydrogel forming polymers) in the eyedrop composition may comprise one or more of the following: a hyaluronic acid, one or more types of hyaluronic acid derivative, a guar gum, one or more types of guar gum derivative, a starch, one or more types of starch derivative, a chitosan, one or more types of chitosan derivative, a chondroitin sulfate, one or more types of chondroitin sulfate derivative, an alginate, one or more types of alginate derivative, a carboxymethylcellulose and one or more types of carboxymethylcellulose derivative. In some embodiments, the polymers (e.g., the hydrogel forming polymers) in the eyedrop composition comprise one or more of the following: a hyaluronic acid, and one or more types of hyaluronic acid derivative.

The polymer (e.g., the hydrogel forming polymer) of the present disclosure may comprise a derivative modified with one or more modifications selected from the group consisting of an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol, an amine, and any combinations thereof. For example, the polymer may comprise one or more polysaccharide derivative, which may be a polysaccharide modified with an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol and/or an amine. In some cases, the polymer may comprise one or more poly acrylic acid derivative, which may be a poly acrylic acid modified with an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol and/or an amine. In some cases, the polymer may comprise one or more poly hydroxyethylmethacrylate derivative, which may be a poly hydroxyethylmethacrylate modified with an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol and/or an amine. In some cases, the polymer may comprise one or more elastin derivative, which may be an elastin modified with an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol and/or an amine. In some cases, the polymer may comprise one or more collagen derivative, which may be a collagen modified with an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol and/or an amine.

In one embodiment, the polymer comprises a derivative of hyaluronic acid modified with one or more thiol groups (HA-SH), in some cases, the HA-SHs may form HA-SH based polymer-polymer type hydrogel under proper conditions. In another embodiment, the polymer comprises a derivative of hyaluronic acid modified with one or more vinylsulfone groups (HA-VS), in some cases, the HA-VSs may form HA-VS based polymer-polymer type hydrogel under proper conditions. In another embodiment, the polymer comprises a derivative of hyaluronic acid modified with one or more thiol groups, as well as a derivative of hyaluronic acid modified with one or more vinylsulfone groups, in some cases, the HA-SH and the HA-VS may react with each other to form polymer-polymer type hydrogel under proper conditions.

In some cases, the derivative may have an average degree of modification (DM) of about 3% to about 50% (for example, about 3% to about 50%, about 4% to about 50%, about 5% to about 50%, about 6% to about 50%, about 7% to about 50%, about 8% to about 50%, about 9% to about 50%, about 10% to about 50%, about 20% to about 50%, about 30% to about 50%, about 40% to about 50%, etc.).

In some cases, the eyedrop composition may comprise at least a first polymer derivative and a second polymer derivative. The first polymer derivative may comprise a first modification and the second polymer derivative may comprise a second modification. The first modification may be different from the second modification. The first polymer derivative may be capable of reacting with the second polymer derivative to form the hydrogel. For example, the first polymer derivative may be a polymer (e.g., a hyaluronic acid) modified with one or more vinylsulfone groups. The second polymer derivative may be a polymer (e.g., a hyaluronic acid) modified with one or more thiol groups.

In some cases, a mass ratio between the first polymer derivative and the second polymer derivative in the composition may be from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10).

In some cases, a molar ratio between the first polymer derivative and the second polymer derivative in the composition may be from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10).

In some cases, a volume ratio between the first polymer derivative and the second polymer derivative in the composition may be from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10).

In some cases, the first polymer derivative may have a first DM, the second polymer derivative may have a second DM, and a ratio between the first DM and the second DM may be from about 10:1 to about 1:10 (e.g., 10:2, 10:3, 10:4, 10:5, 10:6, 10:7, 10:8, 10:9, 1:1, 1:2, 1:3, 1:4, 1:5, 1:6, 1:7, 1:8, 1:9, or 1:10).

In some cases, the first polymer derivative and the second polymer derivative in the composition may have a mass ratio as defined in the present disclosure, a molar ratio as defined in the present disclosure, a volume ratio as defined in the present disclosure, and/or a DM ratio as defined in the present disclosure.

In some cases, the first modification and the second modification may be each independently selected from the group consisting of an acrylate, a maleimide, a vinylsulfone, a N-hydroxysuccinimide, an aldehyde, a ketone, a carbodiimide, a carbonate, an iodoacetyl, a mercaptonicotinamide, a quinone, a thiol, an amine, and any combinations thereof. The first modification and the second modification may be different from each other.

In some cases, the first polymer derivative may be a polymer of the present disclosure modified with one or more vinylsulfone groups (or with a molecule comprising one or more vinylsulfone groups), and the second polymer derivative may be a polymer of the present disclosure modified with one or more thiol groups (or with a molecule comprising one or more thiol groups). The first polymer derivative may be able to react with the second polymer derivative to form the hydrogel.

In an example, the first polymer derivative may be a hyaluronic acid modified with one or more vinylsulfone groups, the second polymer derivative may be a hyaluronic acid modified with one or more thiol groups, and the first polymer derivative may be capable of reacting with the second polymer derivative to form the hydrogel.

In some cases, the first polymer derivative may be a polymer of the present disclosure modified with one or more thiol groups (or with a molecule comprising one or more thiol groups), and the second polymer derivative may be a polymer of the present disclosure modified with one or more vinylsulfone groups (or with a molecule comprising one or more vinylsulfone groups). The first polymer derivative may be able to react with the second polymer derivative to form the hydrogel.

In an example, the first polymer derivative may be a hyaluronic acid modified with one or more thiol groups, the second polymer derivative may be a hyaluronic acid modified with one or more vinylsulfone groups, and the first polymer derivative may be capable of reacting with the second polymer derivative to form the hydrogel.

In some cases, the polymer may have an average molecular weight from about 100,000 to about 5,000,000 dalton (e.g., from about 120,000 to about 5,000,000 dalton, from about 200,000 to about 5,000,000 dalton, from about 300,000 to about 5,000,000 dalton, from about 400,000 to about 5,000,000 dalton, from about 500,000 to about 5,000,000 dalton, from about 600,000 to about 5,000,000 dalton, from about 670,000 to about 5,000,000 dalton, from about 1,000,000 to about 5,000,000 dalton, from about 1,500,000 to about 5,000,000 dalton, from about 2,000,000 to about 5,000,000 dalton, from about 2,500,000 to about 5,000,000 dalton, from about 2,600,000 to about 5,000,000 dalton, from about 3,000,000 to about 5,000,000 dalton, from about 3,500,000 to about 5,000,000 dalton, from about 3,600,000 to about 5,000,000 dalton, from about 2,000,000 to about 4,000,000 dalton, from about 2,500,000 to about 3,500,000 dalton, from about 2,600,000 to about 3,600,000 dalton, from about 1,000,000 to about 2,600,000 dalton, from about 800,000 to about 2,600,000 dalton, from about 700,000 to about 2,500,000 dalton, from about 670,000 to about 2,600,000 dalton, or from about 600,000 to about 2,500,000 dalton).

In some cases, the eyedrop composition may further comprise a cross-linker different from the one or more polymers. For example, the cross-linker may be a small molecule cross-linker, a macromolecule cross-linker, or a combination thereof.

In some cases, the cross-linker may be a small molecule cross-linker. The small molecule cross-linker may comprise a molecule containing a group selected from acrylate, maleimide, vinylsulfone, hydroxysuccinimide, aldehyde, ketone, multi-carbodiimide, carbonate, iodoacetyl, mercaptonicotinamide, quinone, thiol, amine, and any combinations thereof.

In some cases, the cross-linker may be a macromolecule cross-linker. The macromolecule cross-linker may comprise a macromolecule containing a group selected from acrylate, maleimide, vinylsulfone, hydroxysuccinimide, aldehyde, ketone, multi-carbodiimide, carbonate, iodoacetyl, mercaptonicotinamide, quinone, thiol, amine, and any combinations thereof.

In some cases, the cross-linker may be selected from the group consisting of dithiothreitol, di-cysteine, PEG-dithiol, 4 or 8 arm-PEG thiol, divinyl sulfone, Bis(vinylsulfonyl) methane, PEG-VS and 4 or 8 arm-PEGVS.

In a specific example, the polymer is a hyaluronic acid modified with one or more vinylsulfone groups (e.g., HA-VS). The crosslinker is a multi-thiol small molecule, for example DTT, di-cysteine, etc., or a macromolecule having its end groups functionalized with thiol, for example PEG-dithiol or 4 or 8 arm-PEG thiol. By reacting HA-VS with the crosslinker when certain reaction condition is met, HA-VS hydrogel-crosslinker type hydrogel may be formed.

In a specific example, the polymer is a hyaluronic acid modified with one or more thiol groups (e.g., HA-SH). The crosslinker is a multi-vinylsulfone small molecule, for example DVS, Bis(vinylsulfonyl)methane, etc., or macromolecule having its end groups functionalized with VS, for example PEG-VS or 4 or 8 arm-PEGVS. By reacting HA-SH with the crosslinker when certain reaction condition is met, HA-SH hydrogel-crosslinker type hydrogel is formed.

In some cases, the eyedrop composition may not comprise any crosslinker different from the polymers (e.g., the hydrogel forming polymers) therein. For example, the polymers (e.g., hydrogel forming polymers) of the present disclosure may form chemical and/or physical crosslinks among themselves and no additional crosslinker would be comprised in the eyedrop composition. In some embodiments, the eyedrop composition does not comprise any small molecule crosslinker.

The eyedrop composition may comprise a phosphate buffer. For example, the phosphate buffer may be Phosphate Buffered Saline (PBS).

The eyedrop composition may have a pH of about 3.5 to about 9.0 (e.g., about 4.0 to about 9.0, about 4.5 to about 9.0, about 5.0 to about 9.0, about 5.5 to about 9.0, about 6.0 to about 9.0, about 6.5 to about 9.0, about 7.0 to about 9.0, about 7.5 to about 9.0, about 8.0 to about 9.0, about 8.5 to about 9.0, about 7.0 to about 7.8, or about 7.4).

In some cases, the eyedrop composition may be biocompatible. For example, it would exhibit no significant toxicity, injuries, or immunological rejections in a biological (living) tissue or a biological (living) system.

In the present disclosure, the eyedrop composition may be prepared through the following process: providing a composition comprising at least a first polymer derivative and a second polymer derivative, wherein the first polymer derivative comprises a first modification and the second polymer derivative comprises a second modification, the first modification is different from the second modification, and the first polymer derivative is capable of reacting with the second polymer derivative to form the hydrogel. The process may further comprise subjecting the composition to conditions enabling formation of the hydrogel.

In some embodiments, the subjecting comprises incubating the composition at about 30° C. to about 45° C. (e.g., at about 32° C. to about 40° C., at about 35° C. to about 40° C., such as at about 37° C.).

In some cases, the method may comprise cross-linking the polymers in the composition to generate the hydrogel comprised in the eyedrop composition of the present disclosure. For example, the conditions enabling formation of the hydrogel may also enable cross-linking of the polymers in the composition. In some cases, the cross-linking may comprise incubating the polymers in the composition at about 20° C. to about 50° C., about 25° C. to about 50° C., about 30° C. to about 50° C., about 31° C. to about 50° C., about 32° C. to about 50° C., about 33° C. to about 50° C., about 34° C. to about 50° C., about 35° C. to about 50° C., about 36° C. to about 50° C., about 37° C. to about 50° C., about 38° C. to about 50° C., about 39° C. to about 50° C., about 40° C. to about 50° C., or about 45° C. to about 50° C. In some embodiments, the cross-linking comprises incubating the polymers in the composition at a temperature of about 30° C. to about 40° C., e.g., about 35° C. to about 39° C., such as at about 37° C. In some cases, the cross-linking may comprise incubating the polymers in the composition for at least about 1 hour, e.g., for at least about 2 hours, for at least about 3 hours, for at least about 4 hours, for at least about 5 hours, for at least about 6 hours, for at least about 7 hours, for at least about 8 hours, for at least about 9 hours, for at least about 9.5 hours, for at least about 10 hours, for at least about 10.5 hours, for at least about 11 hours, for at least about 12 hours, for at least about 13 hours, for at least about 14 hours, for at least about 15 hours, for at least about 16 hours, for at least about 17 hours, for at least about 18 hours, for at least about 19 hours, for at least about 20 hours, for at least about 24 hours or more.

For example, the method may comprise: 1) preparing a first polymer population (or a first polymer derivative) and a second polymer population (or a second polymer derivative) (e.g., polymers in the first polymer population may comprise hyaluronic acids modified with one or more vinylsulfone groups; and polymers in the second polymer population may comprise hyaluronic acids modified with one or more thiol groups) in water, adjusting the pH (for example, by adding a buffer solution); 2) mixing polymers of the first polymer population (or the first polymer derivative) with those of the second polymer population (or the second polymer derivative) at a pre-set ratio, the concentration of the polymers in the composition is as defined in the present disclosure; and 3) incubating the mixture under conditions allowing formation of the hydrogel according to the present disclosure.

In some cases, the eyedrop composition may be an artificial tear, a contact lens rewetting agent, or a lubricating agent.

In some cases, the eyedrop composition may further comprise a therapeutically active agent, e.g., an agent for treating or alleviating an eye disorder or condition.

In another aspect, the present disclosure relates to a method for treating or alleviating an eye disorder or condition in a subject in need thereof, comprising administering to the subject an effective amount of the eyedrop composition of the present disclosure.

In another aspect, the present disclosure relates to a method for improving ocular comfort or relieving ocular dryness in a subject in need thereof, comprising administering to the subject an effective amount of the eyedrop composition.

The administering may comprise applying one or more drops of the eyedrop composition on or to an area of an eye of the subject. In some cases, the method may comprise administering the eyedrop composition by squeezing an effective amount of the eyedrop composition out of an eyedrop bottle to the cornea surface of the subject.

The subject may comprise human-beings and non-human animals, such as dogs, rabbits or other animals.

In another aspect, the present disclosure relates to the eyedrop composition, for treating or alleviating an eye disorder or condition in a subject in need thereof, and/or for improving ocular comfort or relieving ocular dryness in a subject in need thereof.

In another aspect, the present disclosure relates to use of an eyedrop composition in the manufacture of a product for improving ocular comfort or relieving ocular dryness, and/or for treating or alleviating an eye disorder or condition.

In some cases, eye disorder or condition is selected from the group consisting of a dry eye syndrome and Contact Lens Discomfort.

The eyedrop composition of the present disclosure may have an excellent property of better controlled release of agents (e.g., pharmaceutically active agent) with longer action time, better biocompatibility, longer storage time, and/or good clinical trial results.

EXAMPLES

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., kb, kilobase(s); pl, picoliter(s); s or sec, second(s); min, minute(s); h or hr, hour(s) and the like.

Example 1 Measurement of HA Samples 1.1. Measurement of [η]

[η] can be measured directly using capillary viscometers. For example, three HA samples, namely, sample A, sample B and sample C, were measured by a Ubbelohde viscometer. These HA samples were purchased form Bloomage Freda Biopharm Co. Ltd. (Shandong, China). The polymers were measured by the supplier according to the European Pharmacopeia. Table 1 shows the intrinsic viscosity ([η]) of sample A, sample B and sample C measured by a Ubbelohde viscometer.

TABLE 1

| Intrinsic viscosity ([η]) measured by a Ubbelohde viscometer | | | |
|---|---|---|---|
| | Sample A | Sample B | Sample C |
| Ubbelohde viscometer [η] | 39.2 dL/g | 14 dL/g | 3.7 dL/g |

1.2 Estimation of the Molecular Weight of the Polymers

The molecular weight (MW) of a polymer was calculated from the intrinsic viscosity value measured by Ubbelohde viscometer, using the Mark-Houwink-Sakurada equation:

$$[\eta]=K_M(MW)^a$$

wherein $K_M$ and a (Mark-Houwink-Sakurada exponent) are constants for a given polymer-solvent pair.

The MW of the sample A, B and C was calculated to be 2.6 MDa, 670 KDa and 120 KDa for the sample A, B and C accordingly.

Example 2 Preparation of Polymer Derivatives 2.1 The Preparation of HA-VS

Hyaluronic acids (HA) were modified with pedant VS as described by Yu and Chau (*Biomacromolecules* 2015, 16 (1), 56-65). Briefly, HA was dissolved in deionized water (DI water). The concentration was from 1 mg/ml to 40 mg/ml depending on molecular weight (MW) of HA. For high MW HA (e.g. MW>500 kDa), the concentration was lower (e.g. from 1 mg/ml to 5 mg/ml), for low MW HA (e.g., MW<500 kDa), the concentration was higher (e.g. 5 mg/ml to 40 mg/ml).

After complete dissolution, 5M NaOH was added drop-wise to the polymer solution to a final concentration of 0.1M. Divinylsulfone (DVS) was added instantly with vigorous mixing. Alternatively, DVS was first dissolved in DI water at 1 mg (DVS)/8 ml (water) and added instantly into the vigorously mixing polymers. The molar ratio between DVS and hydroxyl groups (OH) of HA was at least 1.25:1. For low concentration of HA, the molar ratio was 6:1 or higher. The reaction time was chosen depending on the target degree of modification (DM). For a given reaction time, the degree of modification was also depending on the concentration of both HA and DVS, the temperature and the final NaOH concentration.

For the HA sample C (the molecular weight of 120 kDa), the HA concentration was 20 mg/ml, and the molar ratio between DVS and OH of HA was 1.5:1; for the HA sample B (the molecular weight of 670 kDa), the HA concentration was 10 mg/ml, and the molar ratio between DVS and OH of HA was about 3:1; and for the HA sample A (the molecular weight of 2.6 MDa), the HA concentration was 2.5 mg/ml, and the molar ratio between DVS and OH of HA was about 6:1.

The reaction was stopped by adding 6M HCl. The polymers were purified by membrane separation using dialysis bag or tangential flow filtration against DI water (about pH 5.5) or acidic DI water of about pH 4 adjusted by HCl. The purified polymer was stored as a solution at 4° C. For measuring the degree of modification (DM), HA-VS was freeze dried and measured by ¹HNMR.

2.2 The Preparation of HA-SH

Hyaluronic acids (HA) were modified with pedant SH group as described by Yu and Chau (*Biomacromolecules* 2015, 16 (1), 56-65). Briefly, HA was first modified to HA-VS (as described in Example 2.1). The HA-VS solution was purged with $N_2$ for at least 20 minutes. Dithiothreitol (DTT) of 10× molar excess to VS group or the amount needed to make a 0.05M DTT solution (depending on which DTT concentration is higher) was dissolved in water (pH about 5.5) at about 400 mg/ml and purged with $N_2$ for at least 5 minutes and added to the HA-VS solution. The pH of the HA-VS/DTT solution was around 4 and the system was continued to be purged with $N_2$. Afterwards, 0.5M phosphate buffer (PB) of 1/10 the volume of HA-VS was purged with $N_2$ for at least 5 minutes and added to the HA-VS/DTT solution. The reaction was allowed for at least 25 minutes. The reaction was stopped by adding 1M HCl to reduce the pH to 3.5-4.5. The polymers were purified by membrane separation using dialysis bag or tangential flow filtration against DI water, or DI water of pH 4 adjusted by HCl. The purified polymer was stored as a solution at 4° C. The degree of modification (DM) was determined by ¹HNMR and Ellmans' assay for HA-SH.

Figures 1, 2, 3:
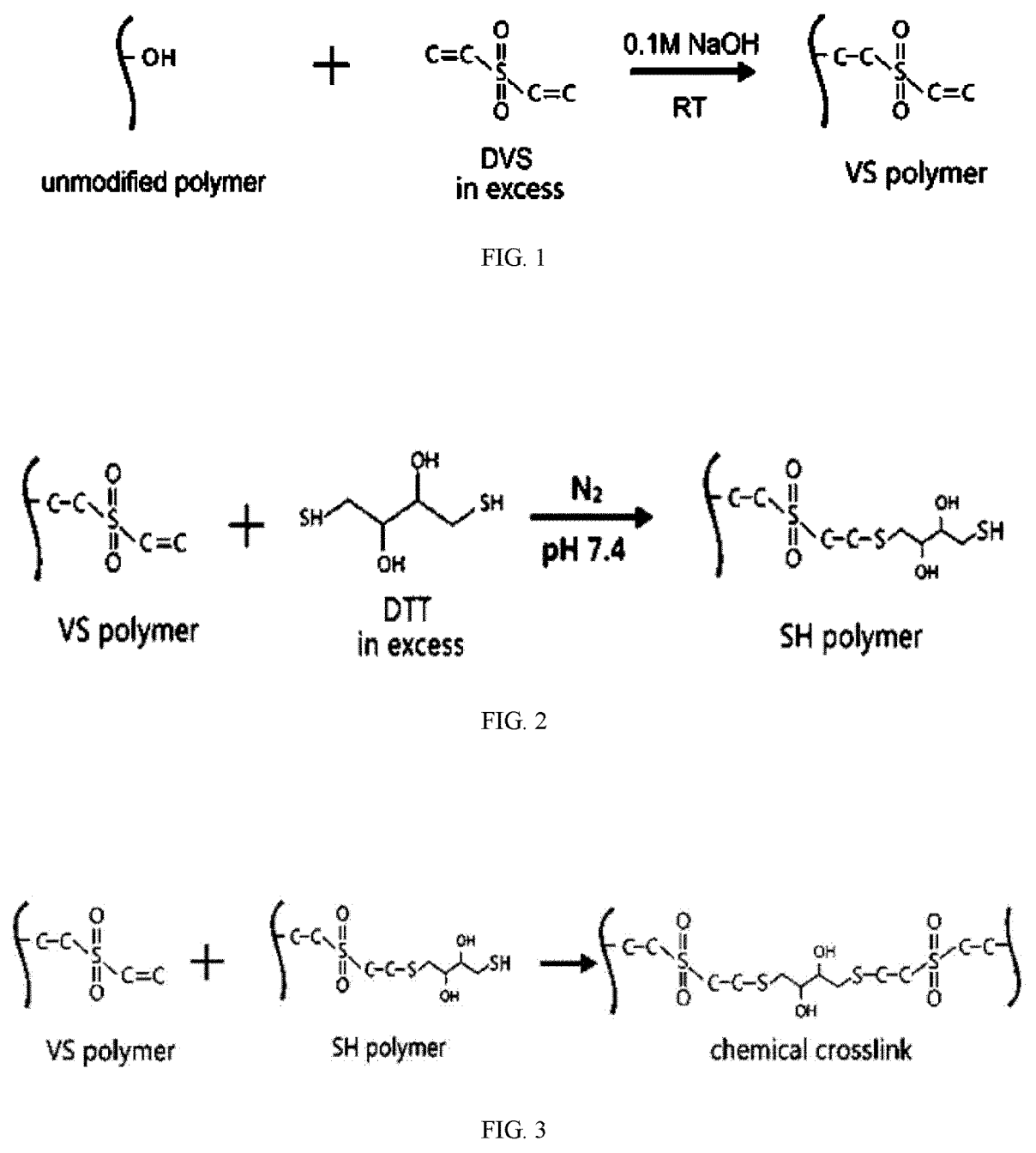

Synthesis of vinylsulfonated hyaluronic acid (HA-VS) was shown in FIG. 1. And thiolated hyaluronic acid (HA-SH) was synthesized according to FIG. 2.

Example 3 Hydrogel Formation 3.1. Formation of HA-VS/HA-SH Based Polymer-Polymer Type Hydrogel The concentration of HA-VS and HA-SH was first determined. The polymer solution of known volume was freeze dried and the dry weight of polymer was measured. The dry polymer was at least 4 mg to ensure accurate measurement. Alternatively, the polymer concentration was measured by CTAB assay as described previously (Oueslati et al., CTAB turbidimetric method for assaying hyaluronic acid in complex environments and under cross-linked form, Carbohydrate Polymers, 2014). HA-VS and HA-SH of known concentration was then adjusted to pH 7.4 by the addition of 0.5M PB. The final concentration of PB was about 0.02M to 0.05M. The osmolality was then adjusted using 25% NaCl. The polymers were then mixed at various target volume ratio and mass ratio, and adjusted to the target concentration by adding phosphate buffered saline (PBS).

The polymers were incubated at 37° C. for at least 10 hours for hydrogel formation. The hydrogel formation reaction is demonstrated in FIG. 3.

For HA polymers with an average molecular weight of about 2.6 MDa, with an intrinsic viscosity [η] of about 39.2 dL/g (as measured by a Ubbelohde viscometer), the concentration of the HA polymers (including both the HA-SH and the HA-VS) for forming the HA-VS/HA-SH based polymer-polymer type hydrogel of the present disclosure can be as low as about 0.4 mg/ml (i.e., water content in the hydrogel is more than about 99.96%).

In the present disclosure, the samples A1, A2, A3, A4, A5, A6, A7, A8 and A9 of HA-SH/HA-VS polymer-polymer type hydrogel were prepared based on HA polymers of Sample A in Example 1.1 (with an average molecular weight of about 2.6 MDa and an intrinsic viscosity [η] of about 39.2 dL/g). For samples A1, A2, A3 and A4, the $C_T$ of the hydrogel forming polymers (e.g., the total concentration of the HA-VS and the HA-SH) was about 1.2 mg/ml, 0.8 mg/ml, 0.5 mg/ml and 0.27 mg/ml, respectively, and the DM of the HA-VS and HA-SH was about 10%, respectively, the molar and mass ratio between HA-VS and HA-SH was 1:1. For Sample A5, the hydrogel was formed by mixing the HA-VS and HA-SH at 1:1 DM ratio and 1:1 mass ratio, the total concentration $C_T$ of the hydrogel forming polymers in the composition was about 0.5 mg/ml, and the DM of the HA-VS and HA-SH was about 20%, respectively. For sample A6, the hydrogel was formed by mixing the HA-VS (with a DM of 8%) and HA-SH (with a DM of 8%) at 1:1 DM ratio and 1:1 mass ratio, the total concentration $C_T$ of the hydrogel forming polymers in the composition was about 0.45 mg/ml. For sample A7, the hydrogel was formed by mixing the HA-VS (with a DM of 30%) and HA-SH (with a DM of 30%) at 1:1 DM ratio and 1:1 mass ratio, the total concentration $C_T$ of the hydrogel forming polymers in the composition was about 0.4 mg/ml. For sample A8, the hydrogel was formed by mixing the HA-VS (with about 10% DM and 0.6 mg/ml) and the HA-SH (with about 5% DM and 0.3 mg/ml) and the $C_T$ is about 0.9 mg/ml. For sample A9, the hydrogel was formed by mixing the HA-VS (with 15% DM and 0.6 mg/ml) and the HA-SH (with 10% DM and 0.3 mg/ml), and the $C_T$ is about 0.9 mg/ml.

The samples B1 and B2 of HA-SH/HA-VS polymer-polymer type hydrogel were prepared based on HA polymers of Sample B in Example 1.1 (with an average molecular weight of about 670 kDa and an intrinsic viscosity [η] of about 14 dL/g). For samples B1 and B2, the $C_T$ of the HA polymers (including both the HA-SH and the HA-VS) was about 1.8 mg/ml and 1.08 mg/ml, respectively. The DM of HA-SH and HA-VS was 30%, and the molar and mass ratio between HA-SH and HA-VS was 1:1.

The sample C1 of HA-SH/HA-VS polymer-polymer type hydrogel was prepared based on HA polymers of Sample C in Example 1.1 (with an average molecular weight of about 120 kDa and an intrinsic viscosity [η] of about 3.7 dL/g). For the sample C1, the $C_T$ of the HA polymers (including both the HA-SH and the HA-VS) was about 3.96 mg/ml. The DM of HA-SH and HA-VS was 30%, and the molar and mass ratio between HA-SH and HA-VS was 1:1.

3.2 Formation of HA-SH Based Polymer-Polymer Type Hydrogel

Sample A of HA polymer (with a weight average molecular weight of about 2.6 MDa, and an intrinsic viscosity [η] of about 39.2 dL/g) was used. HA-SH was prepared according to Example 2.2. The HA-SH was adjusted to pH 7.4 by the addition of 0.5M PB. The final concentration of PB was about 0.02M to 0.05M. The DM of the polymer was about 10%. The polymer was then adjusted to the target concentration by adding phosphate buffered saline (PBS). Sample F of HA-SH polymer-polymer type hydrogel was prepared with a $C_T$ of about 1.7 mg/ml.

The polymers were incubated at 37° C. for at least 10 hours for hydrogel formation.

3.3. Formation of Polymer-Small Molecular Crosslinker Type Hydrogel

DTT was mixed with HA-VS (the HA-VS was prepared based on HA polymer of Sample A) at 3:1 molar ratio (DTT:VS). A hydrogel was formed after 30 minutes. The hydrogel was dialyzed against double deionized water for 2 days and collected. The HA-VS has a weight average molecular weight of about 1.9 MDa, an intrinsic viscosity [η] of about 24.5 dL/g and a total polymer (e.g., hydrogel forming polymer) concentration $C_T$ of about 3.8 mg/ml. The DM of the HA-VS was 20%. The obtained HA-SH/DTT hydrogel was named as Sample H of HA-SH/DTT hydrogel.

Example 4 Hydrogel Characterization 4.1 Modulus of the Prepared Hydrogel Samples
(1) Preparation of Hydrogel Samples for Measurement SH based polymer-polymer type hydrogel) was then loaded onto the lower plate or lower bucket of a cone-plate, double-gap or co-centric cylinder fixture, and the mechanical properties were measured by an Anton Paar rheometer.
(2) The Modulus of HA-VS/HA-SH Based Polymer-Polymer Hydrogels Three samples of HA polymers (i.e., Sample A, B and C described in Example 1.1 and 1.2 above) were modified according to Example 2.1 and 2.2, and the modified polymers were used to form a hydrogel of the present disclosure according to Example 3.1, the hydrogels formed were measured according to Example 4.1. To determine whether the polymers formed a hydrogel instead of remaining as a polymer solution, DMA measurement and/or direct observation (to see whether or not the samples flow like water and cannot be mounted to a DMA machine) was used. For DMA measurement, a higher G' value comparing to G" value (e.g., G"/G'<1) at the linear viscoelastic region (LVR) region was used as an indication for hydrogel formation.

The results are summarized in Table 2 below. The mechanical properties were measured at the LVR region of the gel. The inventors surprisingly found that when the intrinsic viscosity [η] of the hydrogel forming polymers in a composition is relatively high (e.g., at least about 3 dL/g, as measured by a Ubbelohde viscometer), and the total concentration $C_T$ of the hydrogel forming polymers (e.g., the HA-VS and the HA-SH) in the composition was relatively low (e.g., lower than about 5 mg/ml such as 1.2, 0.8, 0.5, 1.8, 1.08 and 3.96 mg/ml), a very soft hydrogel may be formed, as shown by the G' and G" of the hydrogels. The G' and the G" were no more than 10.0 Pa, and G" was less than G', indicating the formation of hydrogel.

TABLE 2

| | Gel formation of different hydrogel formulations | | | |
| MW (Da) | Concentration (mg/ml) | G'(Pa) | G"(Pa) | hydrogel formation |
| --- | --- | --- | --- | --- |
| 2.6M | 1.2 (sample A1) | 3.8 ± 0.09 | 0.13 ± 0.01 | yes |
| (sample A) | 0.8 (sample A2) | 0.87 ± 0.03 | 0.07 ± 0.01 | yes |
| | 0.5 (sample A3) | 0.12 ± 0.01 | 0.03 ± 0.01 | yes |
| | 0.27 (sample A4) | 0.028 ± 0.02 | 0.036 ± 0.03 | no |
| 670k | 1.8 (sample B1) | 17.44 ± 0.49 | 5.33 ± 0.33 | yes |
| (sample B) | 1.08 (sample B2) | 4.70 ± 0.40 | 1.55 ± 0.12 | yes |
| 120k | 3.96 (sample C1) | 40.52 ± 0.39 | 9.03 ± 1.98 | yes |
| (sample C) | | | | |

The hydrogel forming polymers were mixed as described in Example 3, and then the mixed polymers were spread evenly on a mold of 50 m(D)×1 m(H). The mold was adhered to a metal plate by covering the plate with parafilm. The mold with polymers was placed in a humidified chamber, and hydrogel was allowed to form. For hydrogel formation, the polymers were kept at 37° C. for 24 hours. After hydrogel formation (i.e., the HA-VS/HA-SH based polymer-polymer type hydrogel), the whole parafilm-mold-gel assembly was detached from the metal plate and mounted on a 50 mm plate fixture. The mold was then removed, leaving the parafilm and the formed hydrogel on the fixture. Parafilm was then firmly wrapped around a bottom plate. The setup was loaded to a DMA machine (ARES Rheometer, TA Instruments, New Castle, DE), and the mechanical properties were measured with a parallel plate of 50 mm diameter.

Alternatively, the hydrogel forming polymers were mixed as described in Example 3 and then incubating at 37° C. for at least 10 hours (e.g., 24 hours unless specified) in a centrifuge tube. The hydrogel formed (i.e., the HA-VS/HA- FIG. 4 shows the modulus (using frequency sweep test) of the sample A1, A2 and A3 of HA-VS/HA-SH based polymer-polymer type hydrogel prepared according to Example 3.1, the modulus of the hydrogel was measured by a rheometer Anton Paar MCR502 with co-centric double gap fixture. The strain was 1% for all tests.

Figure 5:
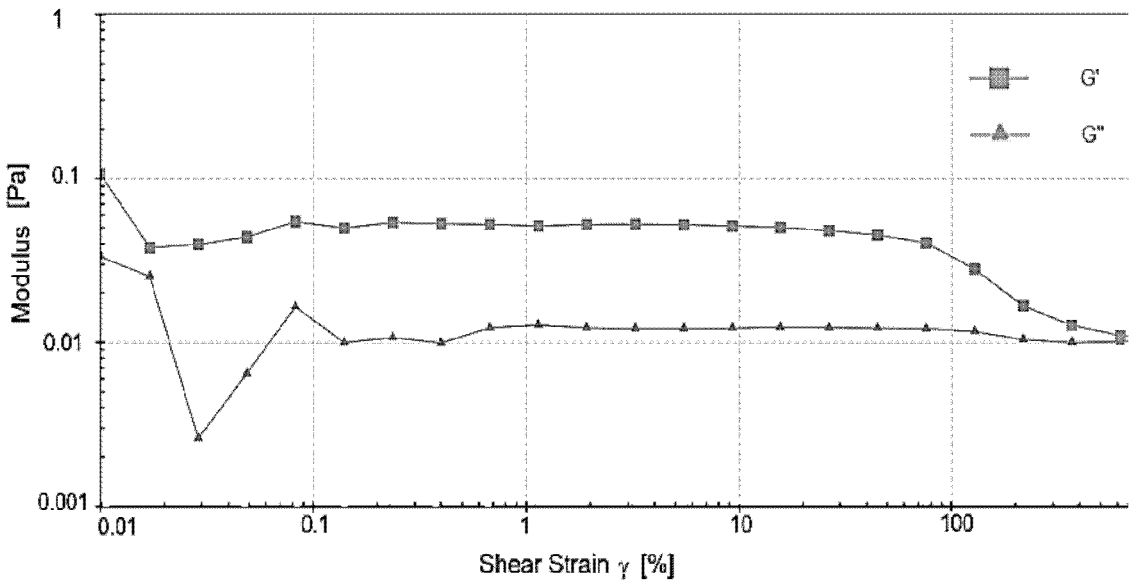
FIG. 5 illustrates the modulus of the hydrogel of the present disclosure.

FIG. 5 shows the modulus (using strain sweep test) of the sample A8 of HA-VS/HA-SH based polymer-polymer type hydrogel prepared according to Example 3.1, using Anton Paar MCR502 with co-centric double gap fixture. The frequency was 1 rad/s. The $C_T$ of sample A8 of HA-VS/HA-SH based polymer-polymer type hydrogel was 0.9 mg/ml, which was lower than 5 mg/ml. Both the G' and G" were no more than 10.0 Pa. And G" was less than G', indicating the formation of hydrogel.

FIG. 6A and FIG. 6B show the modulus and complex viscosity (using strain and frequency sweep test) of the sample A9 of HA-VS/HA-SH based polymer-polymer type hydrogel prepared according to Example 3.1, using Anton Paar MCR302 with 50 mm cone-plate fixture. The frequency was 5 rad/s for strain sweep test and the strain was 5% for frequency sweep test. The $C_T$ of sample A9 of HA-VS/HA-SH based polymer-polymer type hydrogel was 0.9 mg/ml, which was lower than 5 mg/ml. Both the G' and G" were no more than 10.0 Pa. And G" was less than G', indicating the formation of hydrogel.

(3) The Modulus of HA-SH Polymer-Polymer Hydrogel

FIGS. 7A and 7B illustrate the strain sweep test and frequency sweep test of Sample F of HA-SH polymer-polymer type hydrogel of 10% DM prepared according to Example 3.2. In FIG. 7, G', G" and Eta* refer to storage modulus, loss modulus and complex viscosity, respectively. The hydrogel was measured using an Anton Paar MCR 302 rheometer with 50 mm cone-plate fixture. The strain sweep test was measured at 5 rad/s and the frequency sweep test was measured at 5% strain. The $C_T$ of sample F of HA-SH polymer-polymer type hydrogel was 1.7 mg/ml, which was lower than 5 mg/ml. Both the G' and G" were no more than 10.0 Pa. And G" was less than G', indicating the formation of hydrogel.

(4) The Modulus of HA-SH Polymer-Small Molecular Crosslinker Type Hydrogel

FIGS. 8A and 8B illustrate the strain sweep test and frequency sweep test of sample H of HA-SH/DTT hydrogel which was prepared according to Example 3.3. The strain sweep test was measured at 1 rad/s and the frequency sweep test was measured at 5% strain, in which G', G" and Eta* refer to storage modulus, loss modulus and complex viscosity, respectively. The $C_T$ of sample H of HA-SH/DTT hydrogel was 3.8 mg/ml, which was lower than 5 mg/ml. Both the G' and G" were no more than 10.0 Pa. And G" was less than G', indicating the formation of hydrogel.

The results above demonstrate that for all the tested hydrogels, the storage modulus (G') is higher than its corresponding lost modulus (G"), and the value of G' is relatively constant in a dynamic oscillatory shear test at a frequency of from about 0.1 rad/s to about 10 rad/s, indicating that the material is indeed a gel (i.e., a very soft solid-like crosslinked network), instead of a viscous solution.

4.2 The Yield Strain of the Hydrogel

The yield strain can be evaluated by strain sweep tests (FIGS. 5~8). For example, the results in FIG. 5 and FIG. 7 show that the hydrogels had a relatively high yield strain (about 30%) with a low yield stress (about 0.1 to about 1 Pa).

4.3 The Force Requirements for Extruding the Eye Composition of the Present Disclosure In this example, sample A5 of HA-VS/HA-SH based polymer-polymer type hydrogel prepared according to Example 3.1 was used to test the force requirement for extruding the eye composition of the present disclosure.

Commercial artificial tears (e.g. Refresh Plus® and Tears Naturale Free®) or the eyedrop composition of the present disclosure were loaded into a Tears Naturale Free 0.6 ml blow-fill-seal (BFS) single use bottle, respectively. The compressive force required to squeeze the artificial tear or eyedrop composition of the present disclosure out of the bottle was measured by Instron 5567 H1540. Compression test has been performed with 100N load. The force was increased until the first drop was squeezed out of the bottle and at this time, the test was halted immediately. The force required to squeeze the second and the third drop out of respective bottles were performed in the same manner. FIGS. 9A-9C illustrate the force requirement for squeezing the 1st, 2nd and 3rd drop of a Refresh Plus®, a Tears Naturale Free®, and the eyedrop composition of the present disclosure out of the bottles, respectively. It was found that the extrusion force to squeezing the eyedrop composition of the present disclosure out of a Tears Naturale Free 0.6 ml blow-fill-seal (BFS) single use bottle was about 7~16N. These results indicate that the extrusion force required for extruding the eyedrop composition of the present disclosure is similar to that required for extruding the commercial artificial tears.

4.4 The Recovery from Yield of the Hydrogel (1) Strain Sweep Test

With the low yield point, one may have expected that the hydrogel of the present disclosure is mechanically unstable. Surprisingly, the mechanical properties of the hydrogel of the present disclosure can be similar before and after destruction. In this example, sample A3 of HA-VS/HA-SH based polymer-polymer type hydrogel prepared according to Example 3.1 was used to test the recovery from yield of the hydrogel by strain sweep test.

The sample A3 of HA-VS/HA-SH based polymer-polymer type hydrogel was loaded to a co-centric double gap fixture on Anton Paar MCR502. Before and after performing a strain sweep test from 0 to 5000% to destroy the hydrogel, time sweep tests (1% strain and 1 rad/s) were performed to evaluate the modulus of the hydrogel. The hydrogel was equilibrated for about 5 min before each measurement. The G' and G" before destruction was about 0.11 Pa and 0.02 Pa, after destruction was 0.11 Pa and 0.05 Pa. The result shows that the modulus was almost identical before and after destruction.

(2) Extrusion Through an Eye Drop Bottle to Simulate Real-Life Scenario

The hydrogel was also mechanically destroyed by extrusion through an eye drop bottle to simulate real-life scenario. In this example, a special multidose eye drop bottle (Pureflow 1500) from Nemera was used to present a worse-case scenario. The specific design of the cap of the bottle has a long, tortuous and narrower channel for eye drops to travel from the bottle to the outside compared to a regular bottle. The resulting large deformation during extrusion is expected to destroy the hydrogel structure as the yield point of the hydrogel is quite low. And the following hydrogels were used in this example: (1) sample A3 of HA-VS/HA-SH based polymer-polymer type hydrogel prepared according to Example 3.1; (2) samples E of HA-SH/HA-VS polymer-polymer type hydrogel samples prepared according to Example 3.1.

To evaluate the effect of destruction by extrusion on hydrogel mechanical properties, sample A3 and samples E of HA-SH/HA-VS polymer-polymer type hydrogel samples was squeezed from the eye drop bottle (Pureflow 1500) drop by drop to the double gap fixture and the mechanical properties were measured by Anton Paar rheometer. The results of sample A3 and samples E of HA-SH/HA-VS polymer-polymer type hydrogel samples are shown in FIG. 10, respectively. "Before extrusion" indicates that the modulus of the hydrogel was directly measured. "After extrusion" indicates that the modulus of the hydrogel was measured after the hydrogel being extruded from the eyedrop bottles. The results show that squeezing the hydrogels of the present disclosure from the bottle does not alter its modulus significantly.

4.5 The Complex Viscosity of Hydrogels

The frequency sweep test of hydrogels, as shown in FIGS. 6~8, indicates that the complex viscosity of the hydrogel becomes small at a relatively slow frequency (e.g. Eta*<0.01 at frequency about 10-100 rad/s). Since the shear rate of the eye blink is high, at about 50-1200 s⁻¹ (Jossic et al., The fluid mechanics of shear-thinning tear substitutes, J.

Non-Newtonian Fluid Mech. 161 (2009) 1-9), these data indicate that hydrogels made according to the Examples of the present disclosure would be easily spread by blinking after being applied to the eye.

Example 5 Precorneal Retention of the Eyedrop Composition of the Present Disclosure 5.1. Synthesis of VS Reactive Dye The hydrogel of the present disclosure was made fluorescent by tagging a fluorescent dye on the polymer of the present disclosure. A thiol modified fluorescein was used as a dye example. The dye was made by reacting aminofluorescein with N-Acetyl-S-trityl-L-cysteine in DMF, catalyzed by HOBT/HBTU. The product was precipitated in ether for 3 times and dried in vacuum. The dried product was deprotected with a mixture of $TFA:H_2O:TIPS$ (18:1:1) for 1 hour. The final product was precipitated in ether and dried in vacuum and stored at 4° C. The progress of the reaction was determined by mass spectrometry.

5.2. The Fluorescent Dye Conjugation

In one example, HA-VS was adjusted to pH 8.8 by adding 1.5M Tris buffer of pH 8.8 to a final buffer concentration of 0.15M. The solution was purged with $N_2$ for at least 30 minutes. Afterwards, a vinylsulfone reactive dye, either made according to Example 5.1 or purchased from GL Biochem (Shanghai) Ltd. (a cysteine-lysine di-peptide with the amino group of the lysine side chain conjugated with a fluorescein and the amino end group capped by an amide, or AC-Cys-Lys(FAM)), was dissolved in Tris buffer and added to the polymer to react for 12 hours. The molar ratio between the dye and VS group can be up to 1:1 for low DM (e.g. DM=8%) polymer, as the conjugation efficiency is not high, and the reaction will not cover all VS groups. Ideally, at least 80% of VS groups should not be covered by the dye after reaction. The polymer was then dialyzed against DI water adjusted to about pH 4 using HCl. The storage condition for the purified fluorescent-labeled polymer was the same as for HA-VS. Then, the fluorescent-labeled HA-VS was mixed with HA-SH and hydrogels were allowed to form the hydrogel (as described in Example 3).

5.3. Animal Preparation 1.5-year-old NZW rabbits were used for in vivo precorneal retention study. The rabbits were first anesthetized by intramuscular injection (0.8 mL/kg body weight) of a mixture of 2% xylazine/10% ketamine at a ratio of 1:1. When the experiment was conducted longer than one hour, the rabbit was further anesthetized with injection of the xylazine/ketamine mixture at 0.6 mL/kg body weight every hour.

5.4. The Fluorescent Imaging System

Figure 11:
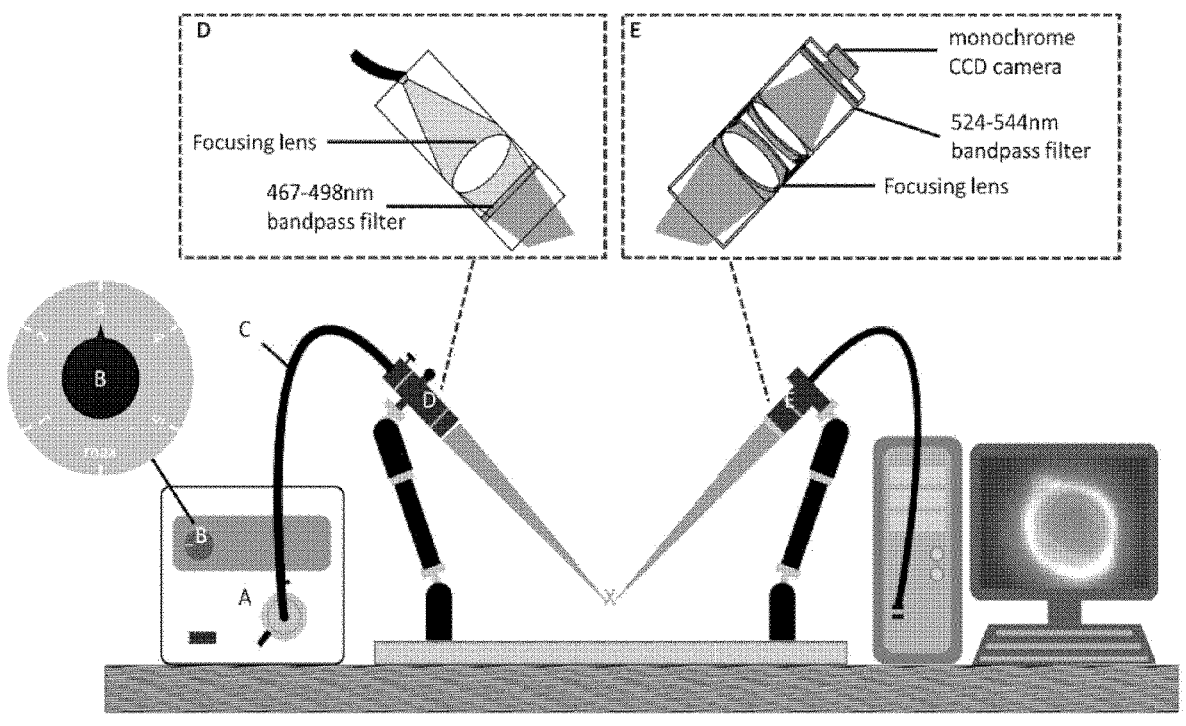
FIG. 11 illustrates the imaging system for measuring the precorneal residence time of the eyedrop composition of the present disclosure.

As illustrated in FIG. 11, the imaging system comprises an excitation module (comprising A, B, C and D) and an emission detection module (comprising E). All components except the lens were purchased from Edmund Optics Singapore Pte. Ltd. (Singapore). All lenses were donated by Newport Corp (U.S.A.). The excitation module comprises a light source (A), which illuminates full spectrum light with adjustable intensity levels (B), a fiber optic cable (C) for light transmission, a focusing lens, and a 467-498 nm bandpass filter (D). The excitation module emits focused blue light illuminating the whole rabbit eye. The 467-498 nm band of wavelengths covers the peak excitation wavelengths for FITC. The emission detection module (E) comprises a 524-544 nm bandpass filter (which covers the emission wavelength of FITC), a focusing lens, and a 1.3-megapixel monochrome CCD camera.

5.5. Detection Range of the Imaging System

Figure 12:
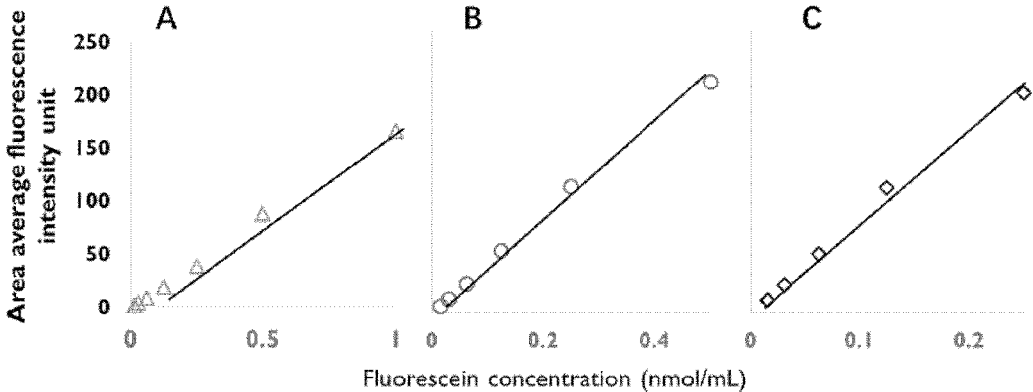
FIGS. 12A~12C illustrate the detection range of the imaging system to measure the precorneal residence time of the eyedrop composition of the present disclosure.

The monochrome CCD camera has a limited range for fluorescent signal detection. Signal that is too strong would saturate the photo sensor, while signal that is too weak cannot be captured. In order to maximize the detection range, images were acquired using at least 2 excitation intensities (one identical to the previous time point and one higher) when the emission intensity was low but still above the detection limit. This procedure could be used to extend the detection range because the emission intensity correlates linearly with dye concentration at all excitation intensity levels. FIGS. 12A~12C illustrate standard curves from the imaging system. Empty triangle: indicates illumination intensity (Ii)=4; Empty circle: Ii=5; Empty diamond: Ii=max. Fluorescent signal intensity was plotted as a function of fluorescein concentrations. F-HA-VS (fluorescent HA-VS, the MW of HA-VS was 29 kDa) dissolved in 0.1M PB (phosphate buffer) was used to prepare serial dilutions for generating the standard curves. The solutions at 50 µL were dispensed in a 96-well plate for fluorescence measurement by the imaging system.

In practice, experiments usually were started at illumination intensity level 4, this allowed the practitioner to follow the fluorescein signal until it diminished to about 1% of its initial fluorescent intensity. The detection limit for fluorescein was 0.01 nmol/ml at maximum illumination intensity. For each experiment, the fluorescent signal intensity at t=0 was defined as 100%. Clearance of polymers over time was presented as percentage change over time. The T1/10, which is the amount of time required for the fluorescence signal falling to one tenth of its initial fluorescence intensity, was calculated based on curve fitting assuming a first order elimination kinetics.

5.6. Hydrogel Application and Fluorescent Signal Detection and Quantification

Retention of fluorescein labeled hydrogel was monitored by imaging the ocular surface at predetermined illumination intensities and time points. Experiments were conducted in a dark room. Before hydrogel or solution was instilled, the background fluorescence of each eye was measured at illumination intensity level 4, 5 and max. Afterwards, 50 µl of hydrogel was instilled onto the center of the cornea. After installation, the eyes were manual blinked to evenly spread the solution or hydrogel on the ocular surface. Appropriate illumination intensity was selected based on the fluorescent signal strength. For example, usually 0-min was imaged using illumination intensity 4. When the fluorescence signal was weak at 7-min, images would be recorded at illumination intensity level 4 and 5 respectively, and the 15-min images would be recorded at illumination intensity level 5 and max. At each intensity-time point, 36 photos were taken using FlyCapture 2.7 (Point Grey Research, Inc., USA), and 5 were randomly selected for fluorescence signal quantification. Images were processed by ImageJ 1.84v. Area average grey-scale signal of whole eye, including the cornea and conjunctiva were measured.

Figure 13:
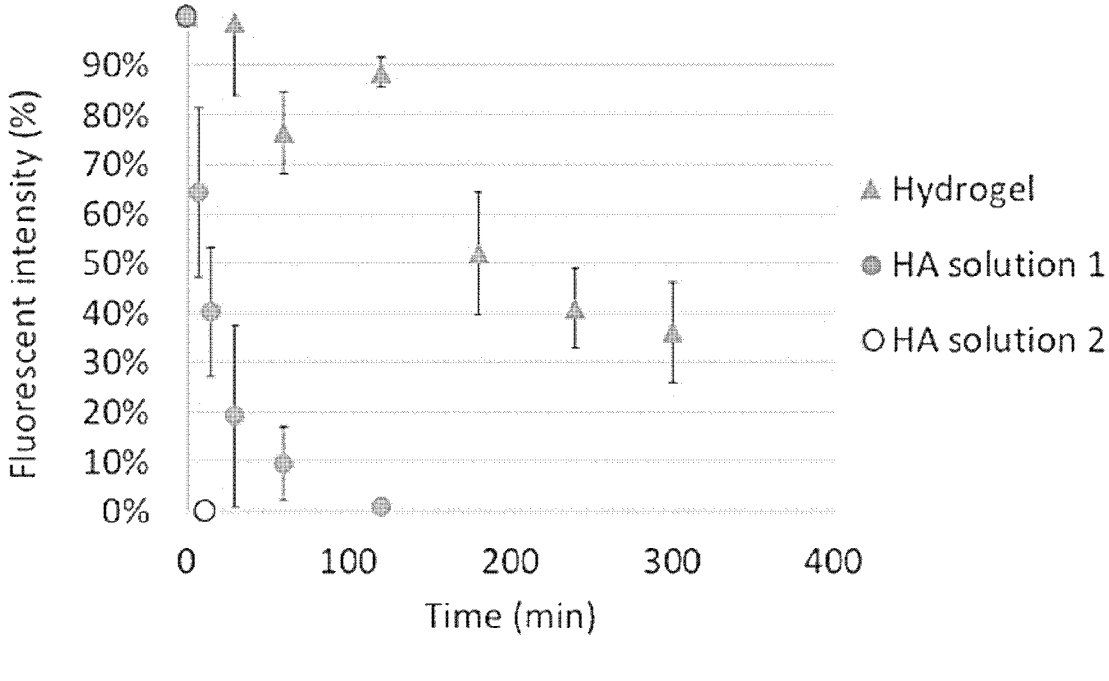
FIG. 13 illustrates the precorneal residence time of the eyedrop composition of the present disclosure.
Figure 14:
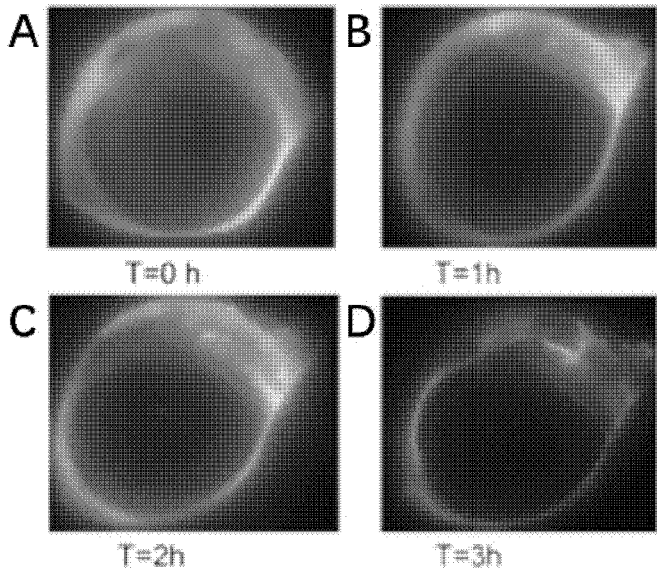
FIGS. 14A~14D illustrate the precorneal residence time of the eyedrop composition of the present disclosure.

In this example, sample A6 of HA-SH/HA-VS polymer-polymer type hydrogel prepared according to Example 3.1 was used except that a fluorescent dye was tagged on the polymer before hydrogel formation. Besides, the clearance behavior of two HA based formulation, a thicker formulation containing 5 mg/ml 1500 kDa HA (HA solution 1) and a thinner formulation containing 0.4 mg/ml 2.6 MDa HA (HA solution 2) was also studied using the current imaging system. The results are illustrated in FIG. 13. As can be seen from FIG. 13, sample A6 of HA-SH/HA-VS polymer-polymer type hydrogel has a clearance rate that is significantly lower than other artificial tears (e.g. HA solution 1 and HA solution 2). About 35% of sample A6 of HA-SH/HA-VS polymer-polymer type hydrogel still remained on the precorneal space after 5 hours. According to Greaves et al., artificial tears commonly exhibit a clearance half-life of about 30 seconds (Greaves et al., A comparison of the precorneal residence of an artificial tear preparation in patients with keratoconjunctivitis sicca and normal volunteer subjects using gamma scintigraphy, ACTA OPHTHALMOLOGICAL, 69 (1991) 432-43). The above results show that the eye composition of the present disclosure exhibits lower clearance rate than other artificial tears or HA based formulation. FIGS. 14A~14D shows representative images of fluorescent labeled sample A6 of HA-SH/HA-VS polymer-polymer type hydrogel at different time points. Strong fluorescent signal was seen at least for 3 hours.

Example 6 Controlled Release of Drug from Hydrogel

Figure 15:
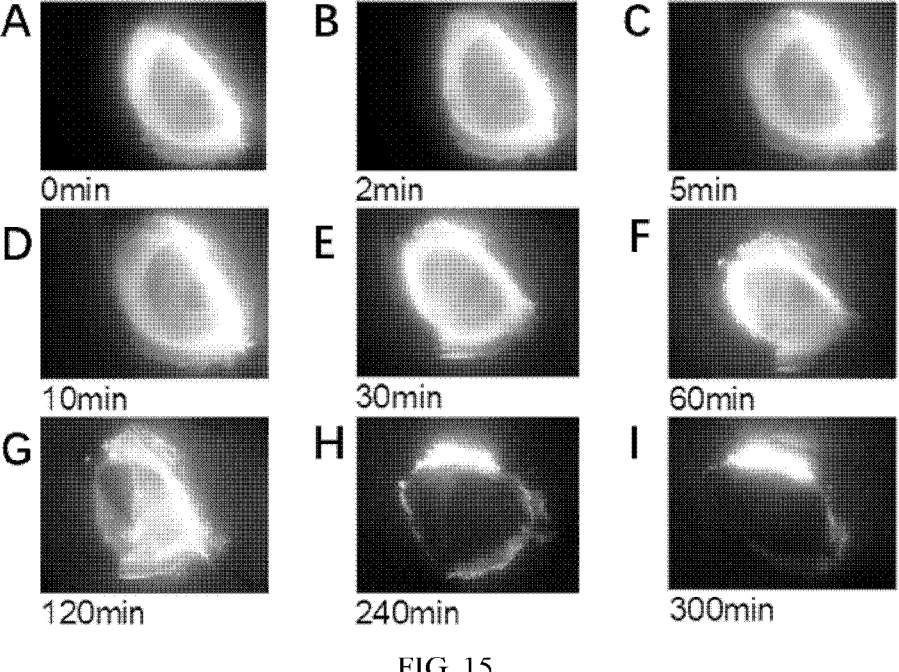
FIGS. 15A~15I illustrate the controlled release of drug of the eyedrop composition of the present disclosure.
Figure 16:
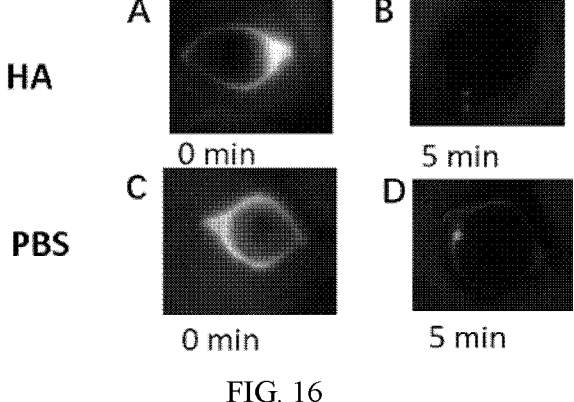
FIGS. 16A~16D illustrate the controlled release of drug of the eyedrop composition of the present disclosure.
Figure 17:
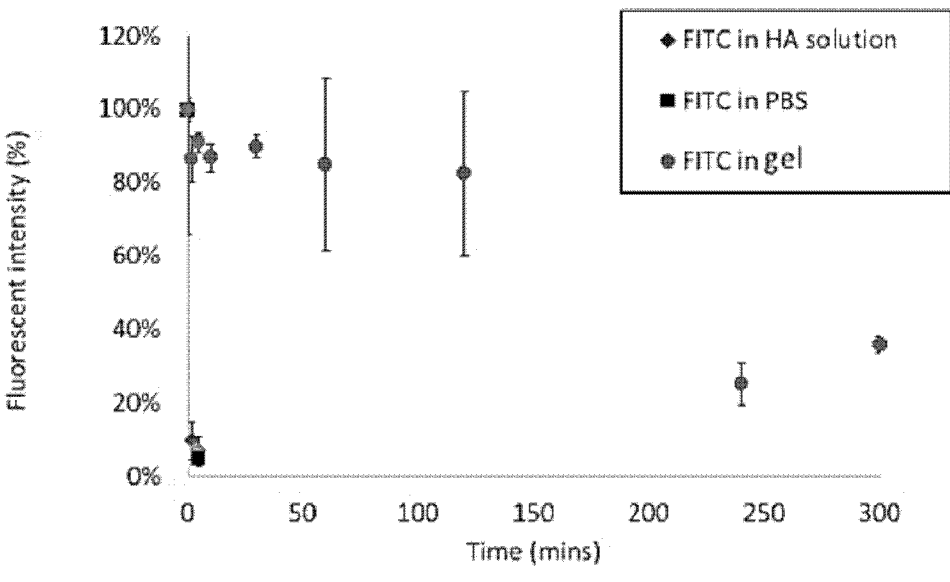
FIG. 17 illustrates the controlled release of drug of the eyedrop composition of the present disclosure.

Retention of model drug fluorescein encapsulated in the hydrogel was monitored by imaging the ocular surface at predetermined illumination intensities and time points. The non-fluorescent labeled hydrogel of sample A7 of HA-SH/HA-VS polymer-polymer type hydrogel was prepared according to Example 3.1, except that non-reactive fluorescein molecule was added before hydrogel formation. Experiments were conducted, and fluorescent signal was measured according to Example 5. The retention data was compared with two controls, the fluorescein molecule dissolved in PBS and HA solution ($C_T$ similar to the hydrogel) instead of encapsulated in hydrogel. FIGS. 15A~15I illustrate the test results of sample A7 of HA-SH/HA-VS polymer-polymer type hydrogel and FIGS. 16A~16D illustrate the test results of the fluorescein molecule dissolved in PBS and HA solution. FIG. 17 shows the fluorescent intensity of sample A7 of HA-SH/HA-VS polymer-polymer type hydrogel and the fluorescein molecule dissolved in PBS and HA solution. FIG. 15 shows that the fluorescent signal of sample A7 was maintained on the eye surface for at least 5 hours, while FIG. 16 shows that the fluorescent signal of fluorescein dissolved in PBS and HA solution disappeared on the ocular surface within 5 minutes. FIGS. 15~17 show that a small molecule encapsulated in a hydrogel of the present disclosure exhibits longer retention of the drug than the molecule dissolved in aqueous solution of PBS buffer or HA.

Example 7 In-Vivo Biocompatibility

Figure 18:
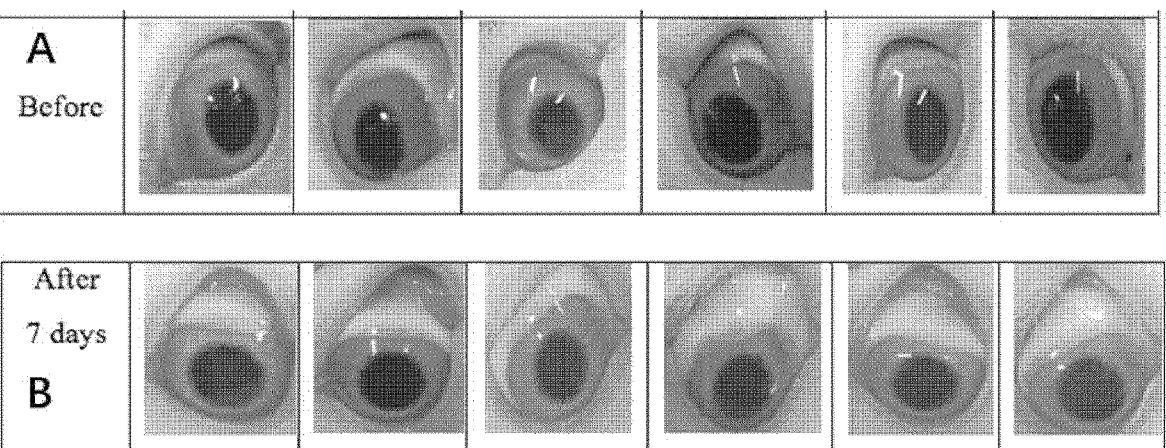
FIGS. 18A and 18B illustrate the in-vivo biocompatibility of the eyedrop composition of the present disclosure.
Figure 19:
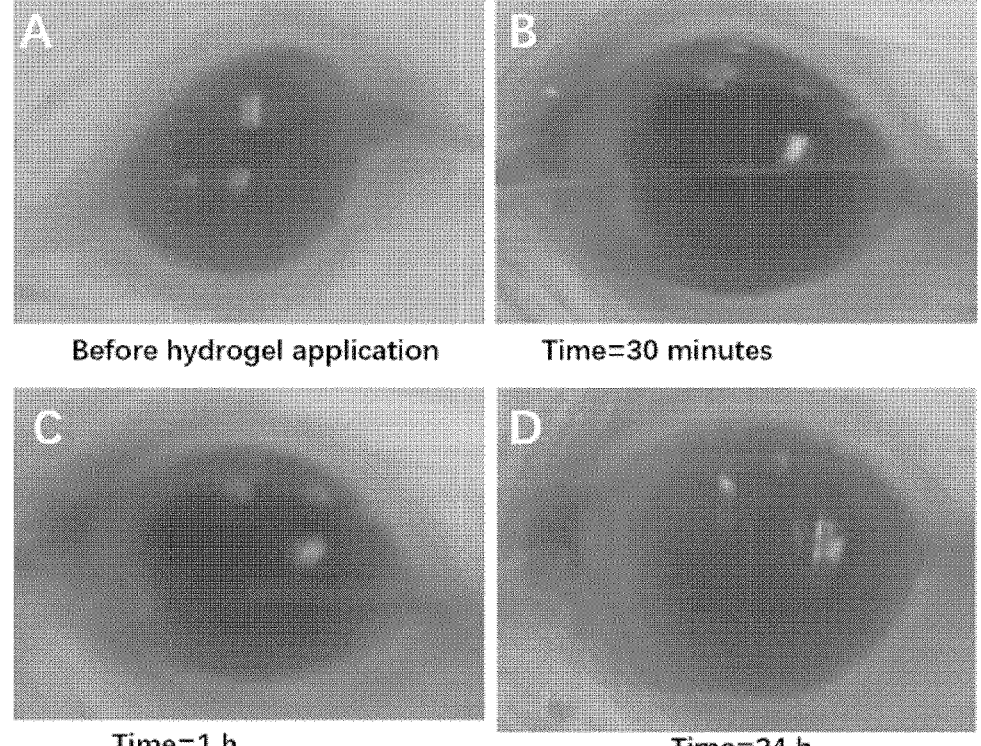
FIGS. 19A~19D illustrate the in-vivo biocompatibility of the eyedrop composition of the present disclosure.
Figure 22:
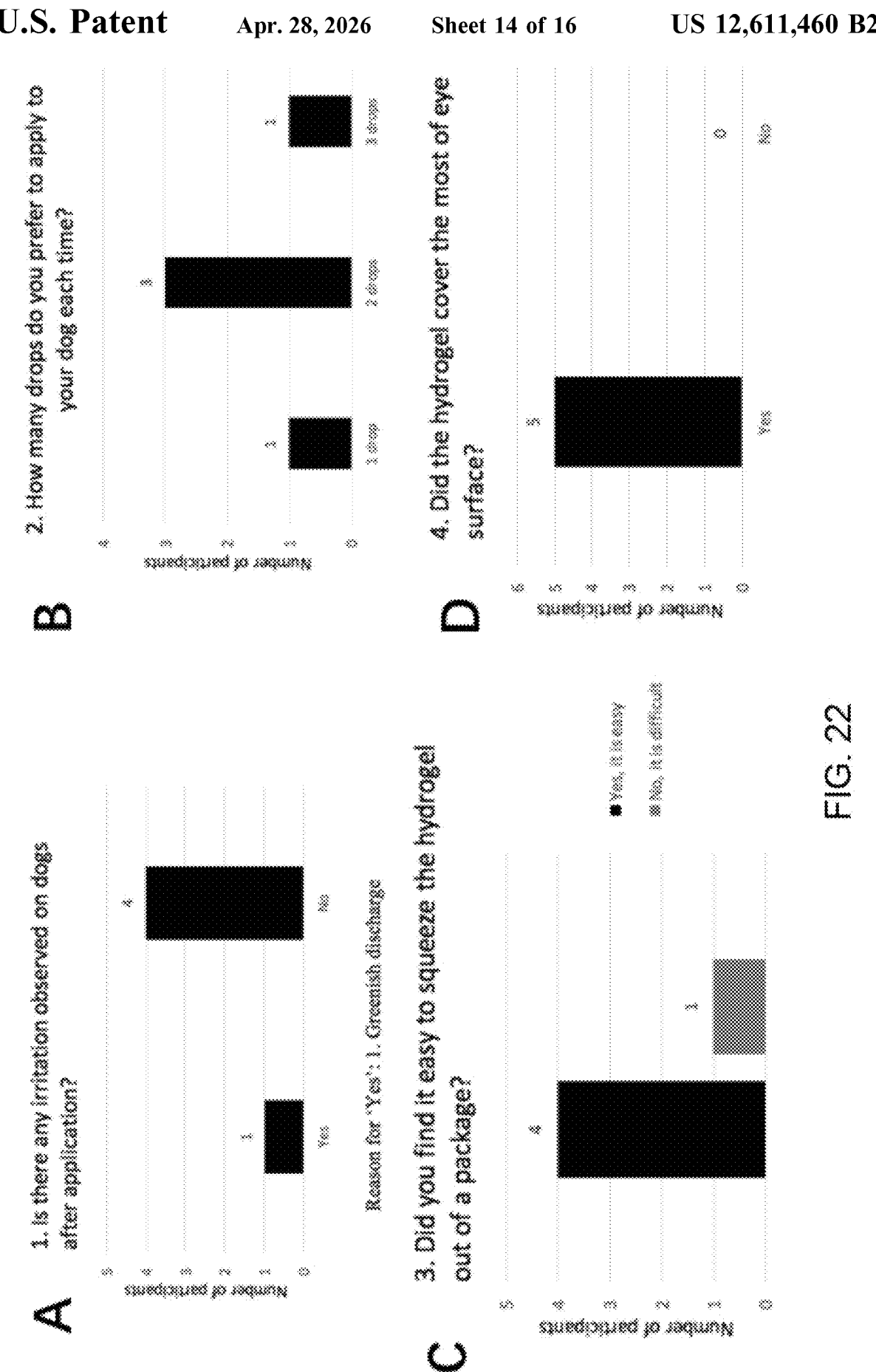
FIGS. 22A~22D illustrate the survey results for subjective assessment of the eyedrop composition of the present disclosure.

In-vivo biocompatibility of the eyedrop composition of the present disclosure was evaluated on the ocular surface of rodents (24 hours) and rabbits (1 week). The test results are shown in FIG. 18. As shown in FIGS. 18A~18B, eyedrop composition comprising sample A7 of HA-SH/HA-VS polymer-polymer type hydrogel was well tolerated. Specifically, the cornea and lens were clear, no inflammation was observed and no sign of ocular discomfort was detected.

Similarly, the eyes of mice were visually inspected before and after the application of the eyedrop composition comprising sample A7 of HA-SH/HA-VS polymer-polymer type hydrogel prepared according to Example 3.1. The eyes were monitored for up to 24 hours after the hydrogel instillation and no gross response such as hyperemia or whitening of cornea has been observed, as shown in FIGS. 19A~19D.

Example 8 In-Vitro Biocompatibility of Hydrogel

To evaluate the in vitro biocompatibility, hydrogels similar to the present disclosure were incubated with ocular cells ARPE19 and tested by Live/Dead assay. To challenge the biocompatibility, hydrogel was prepared with HA-VS and HA-SH of 29 kDa, 20% DM, the mass ratio/molar ratio and volume ratio between HA-VS and HA-SH was 1:1, and the $C_T$ was about 15% concentration. And then the obtained hydrogel was incubated with the cells for 1 day. The concentration was about 300 times higher than the concentration of the present disclosure used in animal studies. It was found that the hydrogel was compatible to ocular cells with over 99.5% cells were stained live in all 5 repeats, as shown FIGS. 20A~20C.

Example 9 Biocompatibility Study of the Hydrogel in Healthy Subjects

This study was carried out with a veterinary ophthalmology specialist. 5 healthy dogs were recruited for the study. Sample A9 of the HA-SH/HA-VS polymer-polymer type hydrogel prepared according to Example 3.1 was used. The dogs were instilled with eyedrop composition comprising the sample A9 of the HA-SH/HA-VS polymer-polymer type hydrogel twice a day, once in the morning and once in the evening for a course of 6 days. The amount of the eyedrop composition applied were varied, 250 µl for days 1-2, 200 µl for days 3-4, and 80 µl for days 5-6, respectively. The survey questions as shown in FIG. 21 were also distributed to pet owners for subjective assessment of the tested eyedrop composition regimen.

The survey results are shown in FIGS. 22A~22D. It was found that the eyedrop composition comprising the hydrogel of the present disclosure was well tolerated by the dogs and well received by the pet owner. In regard to the adverse event, one owner observed a greenish discharge after application of the eyedrop composition, which was determined by the veterinary specialist as unrelated to the application of the hydrogel/eyedrop composition of the present disclosure. Besides, most of the pet owners found it easy to squeeze the hydrogel out of a package. And all the pet owners found that the hydrogel could cover the most of eye surface.

Example 10 Canine Clinical Trial of the Eyedrop Composition

This study was carried out with a veterinary ophthalmology specialist. Dog patients that were diagnosed with dry eye syndrome and have been on 4-6 times a day artificial tear in combination with cyclosporine treatment for over 1 year were enrolled in the study. Based on the clinical outcome of the previous cyclosporine treatment, patients were divided into two groups, cyclosporine responsive group and cyclosporine nonresponsive group. Both groups were switched to twice a day eyedrop hydrogel of the present disclosure (comprising of sample A9 of HA-SH/HA-VS polymer-polymer type hydrogel samples prepared according to Example 3.1)) in combination with cyclosporine. Seven clinical signs including blepharospasm, discharge, corneal staining and Schirmer's test were scored by the specialist at the initiation of the study and right after 1-month treatment with hydrogel. The grading scale is shown in Table 3.

TABLE 3

| Grading scale utilized in the study Clinical sign and symptom | | | | |
| --- | --- | --- | --- | --- |
| Scale | 0 | 1 | 2 | 3 |
| Discomfort (Blepharospasms) | none | seldom | intermittent | constant |
| Conjunctival Hyperemia | none | mild | moderate | severe |
| Cornea (Keratitis) | none | limbal | 50% of cornea | complete |
| Cornea (Pigmentation) | none | peripheral | 50% of cornea | complete |
| Discharge | none | Thickened but not discoloured | purulent | Purulent with dry discharge adhered to thecornea |
| Schirmer's test | ~15 | 10 to 15 | 5 to 10 | <5 |
| Corneal staining | None to mild | variable | Marked central | Severe punctate erosions |

Figure 23:
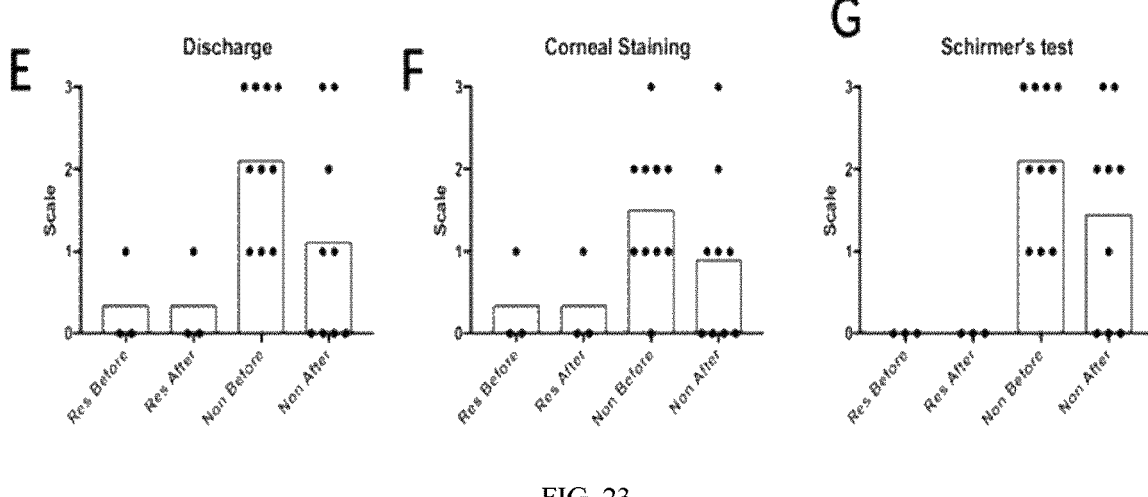
FIGS. 23A~23G illustrate the therapeutic effect of the eyedrop composition of the present disclosure.

It was found that the eyedrop composition/hydrogel of the present disclosure was well tolerated by all dogs and well received by dog owners because the eyedrop composition of the present disclosure require less frequency of instillation with reduced number of instillations from 6 times a day to 2 times a day. The clinical results show that hydrogel was able to maintain the therapeutic effect over the test period (as shown in FIG. 23). In FIGS. 23A-23G, "Res before" refers to cyclosporine responsive patients before the application of the eyedrop composition of the present disclosure. "Res after" refers to cyclosporine responsive patients after the application of the eyedrop composition of the present disclosure. "Non before" refers to cyclosporine non-responsive patients before the application of the eyedrop composition of the present disclosure. "Non after" refers to cyclosporine non-responsive patients after the application of the eyedrop composition of the present disclosure. The grading of each patient was presented in the figure, the bar gives the average value of all patients. It was found that for at least some dogs, clinical signs were improved after the 1-month treatment.

Figure 24:
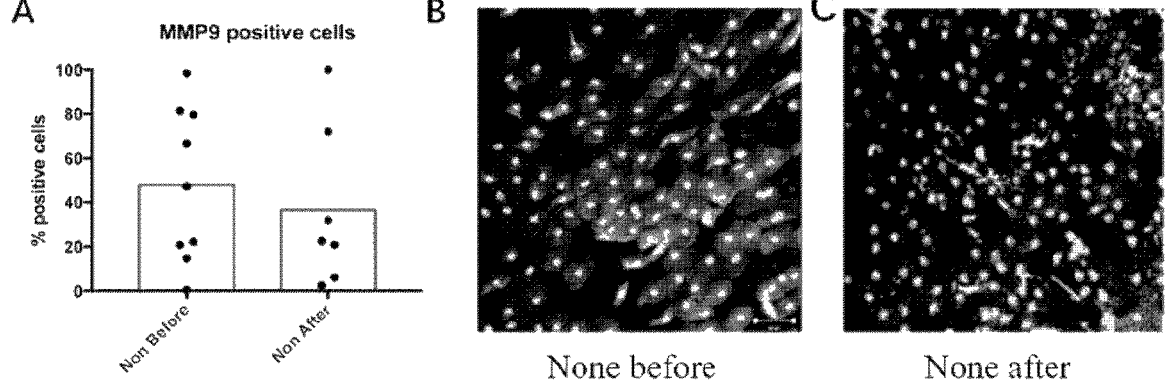
FIGS. 24A~24C illustrate the therapeutic effect of the eyedrop composition of the present disclosure.

To evaluate the effect of new treatment on cellular level, conjunctival cells was collected from dog patients by utilizing impression cytology (IC). A filter paper cut into semicircle shape was sterilized by autoclave. Before the treatment and 1 month after treatment, the filter paper was pressed onto the conjunctival of the patient for about 1 seconds, and immediately fixed in 4% paraformaldehyde. The collected cells were stained immunochemically for MMP-9, an inflammatory marker associated with dry eye disease. The results are shown in FIGS. 24A~24C. "None Before" refers to cyclosporine non-responsive patients before the application of the eyedrop composition of the present disclosure. "None after" refers to cyclosporine non-responsive patients after the application of the eyedrop composition of the present disclosure. The gradings of each patient were presented in FIG. 24A, and the bar shows the average value of all patients. FIG. 24A shows that the hydrogel was able to slightly decrease the level of inflammation even for cyclosporine unresponsive dogs. FIGS. 24B~24C show the staining images of inflammatory markers (the weak fluorescent signal around the strong fluorescent signal of the cell nucleus) in the cell (wherein the nucleus were stained with strong fluorescent signal) of one dog before and after hydrogel application for 1 month. Significant reduction in inflammatory cells was observed.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An eyedrop composition, comprising: a hydrogel forming polymer having an intrinsic viscosity [$\eta$] of at least 3 dL/g in the composition as measured by a Ubbelohde viscometer, wherein a concentration $C_T$ of hydrogel forming polymers in the composition is 0.3-5 mg/mL, and at least some of the hydrogel forming polymers are comprised in the composition in a hydrogel form, and a storage modulus G' of the hydrogel is greater than a loss modulus G" of the hydrogel as measured in a dynamic oscillatory shear test at a given frequency from 0.1 to 1 rad/s at 1% strain, wherein the hydrogel forming polymer comprises a first polymer derivative and a second polymer derivative, wherein the first polymer derivative is a hyaluronic acid modified with one or more vinylsulfone groups, and wherein the second polymer derivative is a hyaluronic acid modified with one or more thiol groups.

2. The composition of claim 1, wherein the hydrogel has at least one of the following:

1) A storage modulus G' of no more than 10.0 Pa, as measured in a dynamic oscillatory shear test;

2) a loss modulus G" of no more than 10.0 Pa, as measured in a dynamic oscillatory shear test;

3) A complex viscosity of no more than 0.2 Pa·s as measured in a dynamic oscillatory shear test at a frequency of less than 100 rad/s;

4) an extrusion force in a range of from 4 N to 45 N, when the hydrogel is squeezed out of a Tears Naturale Free 0.6 ml blow-fill-seal (BFS) single use bottle; and 5) A yield strain of at least 10%, as measured in a dynamic oscillatory strain sweep test.

3. The composition of claim 1, wherein the hydrogel forming polymer is hydrophilic and/or water soluble.

4. The composition of claim 1, wherein the first polymer derivative and/or the second polymer derivative has an average degree of modification (DM) in a range of from 3% to 50%.

5. The composition of claim 1, wherein a molar ratio between the first polymer derivative and the second polymer derivative in the composition is in a range of from 10:1 to 1:10.

6. The composition of claim 1, wherein the first polymer derivative has a first DM, wherein the second polymer derivative has a second DM, and wherein a ratio between the first DM and the second DM is in a range of from 10:1 to 1:10.

7. The composition of claim 1, further comprising:

a cross-linker different from the hydrogel forming polymer, wherein the cross-linker is a small molecule cross-linker, a macromolecule cross-linker, or a combination thereof.

8. The composition of claim 7, wherein the cross-linker is a small molecule cross-linker comprising a molecule comprising an acrylate, maleimide, vinylsulfone, hydroxysuccinimide, aldehyde, ketone, multi-carbodiimide, carbonate, iodoacetyl, mercaptonicotinamide, quinone, thiol, amine, or any combination thereof.

9. The composition of claim 7, wherein the cross-linker is a macromolecule cross-linker comprising a macromolecule comprising an acrylate, maleimide, vinylsulfone, hydroxysuccinimide, aldehyde, ketone, multi-carbodiimide, carbonate, iodoacetyl, mercaptonicotinamide, quinone, thiol, amine, and any combinations thereof.

10. The composition of claim 1, comprising no cross-linker different from the hydrogel forming polymer.

11. A method for treating or alleviating an eye disorder or condition in a subject in need thereof, the method comprising:

administering to the subject an effective amount of the eyedrop composition of claim 1.

12. A method for improving ocular comfort or relieving ocular dryness in a subject in need thereof, the method comprising:

administering to the subject an effective amount of the eyedrop composition of claim 1.

* * * * *